US008952193B2

United States Patent
Davis, Jr.

(10) Patent No.: US 8,952,193 B2
(45) Date of Patent: Feb. 10, 2015

(54) CARBON DIOXIDE SCRUBBING USING IONIC MATERIALS

(71) Applicant: James H. Davis, Jr., Mobile, AL (US)

(72) Inventor: James H. Davis, Jr., Mobile, AL (US)

(73) Assignee: University of South Alabama, Mobile, AL (US)

( * ) Notice: Subject to any disclaimer, the term of this patent is extended or adjusted under 35 U.S.C. 154(b) by 0 days.

(21) Appl. No.: 14/029,298

(22) Filed: Sep. 17, 2013

(65) Prior Publication Data

US 2014/0170054 A1    Jun. 19, 2014

Related U.S. Application Data

(62) Division of application No. 12/594,442, filed as application No. PCT/US2008/059099 on Apr. 2, 2008, now Pat. No. 8,536,371.

(60) Provisional application No. 60/909,538, filed on Apr. 2, 2007, provisional application No. 60/990,128, filed on Nov. 26, 2007.

(51) Int. Cl.
*C07C 317/04*      (2006.01)
*C07C 317/06*      (2006.01)
(Continued)

(52) U.S. Cl.
CPC ............ *C01B 31/20* (2013.01); *B01D 53/1475* (2013.01); *B01D 53/1493* (2013.01); *B01D 53/78* (2013.01); *B01D 2257/302* (2013.01); *B01D 2257/404* (2013.01); *B01D 2257/504* (2013.01); *C07C 211/63* (2013.01); *C07C 309/14* (2013.01); *Y02C 10/06* (2013.01)

USPC .................................... 562/8; 562/35; 562/58

(58) Field of Classification Search
USPC ................................. 562/8, 35, 58
See application file for complete search history.

(56) References Cited

U.S. PATENT DOCUMENTS

| 6,579,343 | B2 | 6/2003 | Brennecke et al. |
| 2002/0189444 | A1 | 12/2002 | Brennecke et al. |
| 2004/0035293 | A1 | 2/2004 | Davis |

FOREIGN PATENT DOCUMENTS

| WO | WO-2004/016570 | * 2/2004 | ............ C07C 309/00 |
| WO | WO-2004/016570 A2 | 2/2004 | |

(Continued)

OTHER PUBLICATIONS

International Search Report from PCT/US2008/059099 dated Nov. 5, 2008.

*Primary Examiner* — Kamal Saeed
*Assistant Examiner* — Janet L Coppins
(74) *Attorney, Agent, or Firm* — Dana M. Gordon; Foley Hoag LLP

(57) ABSTRACT

One aspect of the present invention relates to amine-functionalized task-specific ionic liquids (TSILs). In certain embodiments, the ionic liquids of the invention comprise beta-hydroxy amines, aryl amines or tertiary amines. The TSILs may be used for gas capture, capitalizing on their non-volatile nature. In certain embodiments, the captured gas is selected from the group consisting of $CO_2$, $SO_2$, $CS_2$, and $NO_2$. Another aspect of the present invention relates to a library of $CO_2$-philic salts, which library facilitates reactive gas separation. In certain embodiments, the $CO_2$-philic salts are $CO_2$-reactive TSILs. In certain embodiments, the $CO_2$-philic salts are resinous or plastic in nature.

21 Claims, 20 Drawing Sheets

(51) Int. Cl.

*C01B 31/20* (2006.01)
*B01D 53/14* (2006.01)
*B01D 53/78* (2006.01)
*C07C 211/63* (2006.01)
*C07C 309/14* (2006.01)

(56) References Cited

FOREIGN PATENT DOCUMENTS

WO    WO-2004/113275 A2    12/2004
WO    WO-2004/113275 A2 *    12/2004    ............ C07C 309/00

* cited by examiner

Figure 2
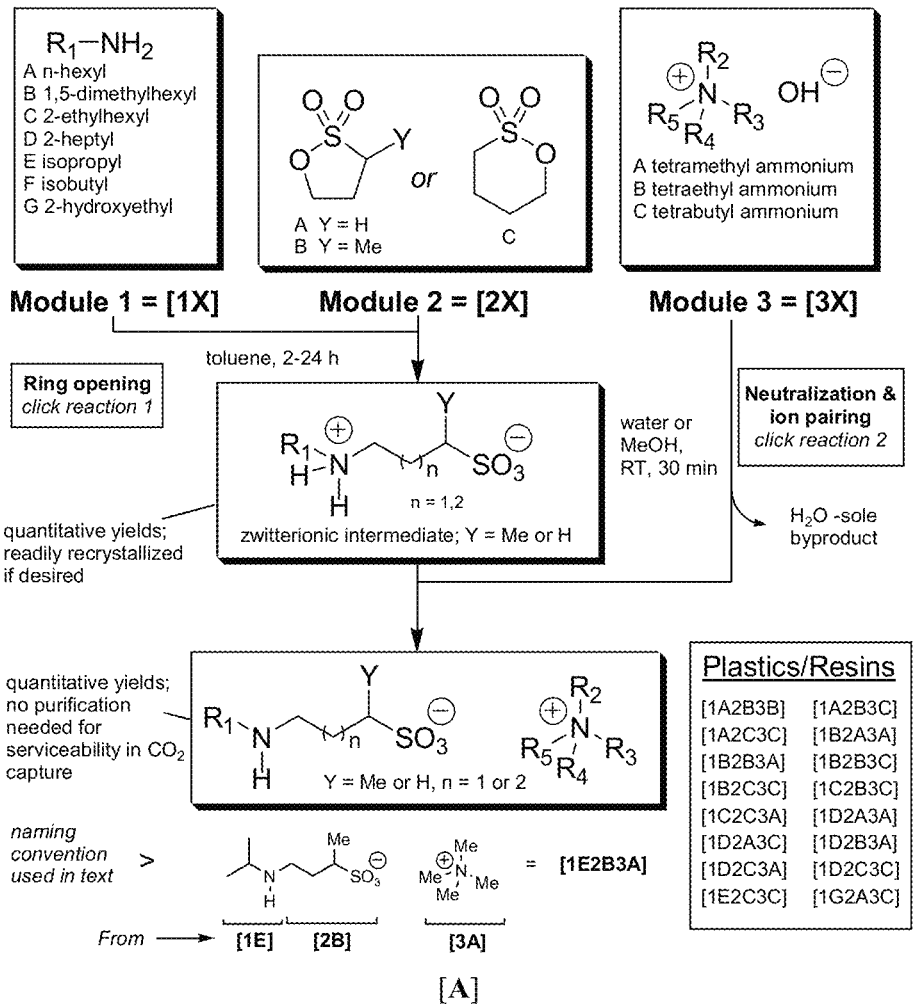
[A]
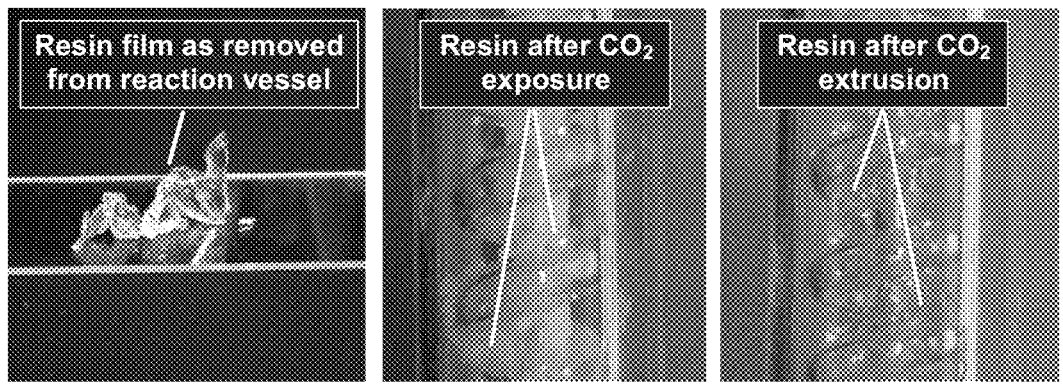
[B]

Figure 4

| Compound | Physical State as Initially Isolated L = liquid; R = plastic or resin/gel; S = solid | $\nu_{CO}$ (cm$^{-1}$, neat, dried in vacuo over P$_2$O$_5$, after exposure to CO$_2$) | $\nu_{CO}$ (cm$^{-1}$, neat, after saturation humidification, resinous/plastic/gel materials) |
|---|---|---|---|
| 1A2A3A | L | 1647 | N/A |
| 1A2A3B | L | 1647 | N/A |
| 1A2A3C | L | 1647 | N/A |
| *1A2B3A* | *S* | *N/A* | *N/A* |
| 1A2B3B | R | 1648 | N/A |
| 1A2B3C | R | 1647 | N/A |
| *1A2C3A* | *S* | *N/A* | *N/A* |
| 1A2C3B | L | 1647 | N/A |
| 1A2C3C | R | 1646 | N/A |
| 1B2A3A | R | 1653 | 1645 |
| 1B2A3B | L | 1653 | N/A |
| 1B2A3C | L | 1637 | N/A |
| 1B2B3A | R | 1646 | N/A |
| 1B2B3B | L | 1647 | 1647 |
| 1B2B3C | R | 1647 | 1647 |
| *1B2C3A* | *S* | *N/A* | *N/A* |
| 1B2C3B | L | | N/A |
| 1B2C3C | R | | 1647 |
| 1C2A3A | | | N/A |
| 1C2A3B | L | 1653 | N/A |
| 1C2A3C | L | 1653 | N/A |

Figure 5

| Compound | Physical State as Initially Isolated L = liquid; R = plastic or resin/gel; S = solid | $\nu_{CO}$ ($cm^{-1}$, neat, dried in vacuo over $P_2O_5$, after exposure to $CO_2$) | $\nu_{CO}$ ($cm^{-1}$, neat, after saturation humidification, resinous/plastic/gel materials) |
|---|---|---|---|
| *1C2B3A* | S | N/A | N/A |
| 1C2B3B | L | 1644 | N/A |
| 1C2B3C | R | 1644 | N/A |
| 1C2C3A | R | 1648 | N/A |
| 1C2C3B | L | 1648 | N/A |
| 1C2C3C | L | 1648 | N/A |
| 1D2A3A | R | 1646 | N/A |
| 1D2A3B | L | 1622 | N/A |
| 1D2A3C | R | 1654 | N/A |
| 1D2B3A | R | 1644 | 1646 |
| 1D2B3B | L | 1645 | N/A |
| 1D2B3C | L | 1645 | N/A |
| 1D2C3A | R | 1647 | 1647 |
| 1D2C3B | L | 1646 | N/A |
| 1D2C3C | R | 1646 | N/A |
| 1E2A3A | L | 1646 | N/A |
| 1E2A3B | L | 1619 | N/A |
| 1E2A3C | L | 1652 | N/A |
| 1E2B3A | L | 1646 | N/A |
| 1E2B3B | L | 1647 | N/A |
| 1E2B3C | L | 1646 | N/A |
| *1E2C3A* | S | N/A | N/A |
| 1E2C3B | L | 1647 | N/A |
| 1E2C3C | R | 1645 | N/A |

Figure 6

| Compound | Physical State as Initially Isolated<br>L = liquid;<br>R = plastic or resin/gel;<br>S = solid | $\nu_{CO}$ (cm$^{-1}$, neat, dried in vacuo over $P_2O_5$, after exposure to $CO_2$) | $\nu_{CO}$ (cm$^{-1}$, neat, after saturation humidification, resinous/plastic/gel materials) |
|---|---|---|---|
| *1F2A3A* | S | N/A | N/A |
| 1F2A3B | L | 1621 | N/A |
| 1F2A3C | L | 1637 | N/A |
| *1F2B3A* | S | N/A | N/A |
| 1F2B3B | L | 1641 | N/A |
| 1F2B3C | L | 1643 | N/A |
| 1F2C3A | L | 1637 | N/A |
| 1F2C3B | L | 1647 | N/A |
| 1F2C3C | L | 1641 | N/A |
| *1G2A3A* | S | N/A | N/A |
| 1G2A3B | L | 1653 | N/A |
| 1G2A3C | R | 1637 | 1647 |
| 1G2B3A | L | 1647 | N/A |
| 1G2B3B | L | 1647 | N/A |
| 1G2B3C | L | 1647 | N/A |
| 1G2C3A | L | 1642 | N/A |
| 1G2C3B | L | 1647 | N/A |
| *1G2C3C* | S | N/A | N/A |

Figure 7

| Compound | Molecular Weight | IL mass (g) | IL moles |
|---|---|---|---|
| 1B2A3A | 324 | 0.0935 | 0.000289 |
| 1B2A3B | 380 | 0.0783 | 0.000206 |
| 1B2A3C | 492 | 0.0824 | 0.000167 |
| 1B2B3B | 394 | 0.0829 | 0.00021 |
| 1B2B3C | 506 | 0.0637 | 0.000126 |
| 1B2C3C | 506 | 0.0959 | 0.00019 |
| 1D2A3A | 310 | 0.0276 | 8.9E-05 |
| 1D2A3C | 478 | 0.0393 | 8.22E-05 |
| 1D2C3A | 324 | 0.0276 | 8.52E-05 |
| 1G2A3C | 424 | 0.0785 | 0.000185 |

| Compound | Day 1 | | Day 4 | | Day 7 | | Day 14 | |
|---|---|---|---|---|---|---|---|---|
| | mass (g) | mol | mass (g) | mol | mass (g) | mol | mass (g) | mol |
| 1B2A3A | 0.0173 | 0.000961 | 0.0605 | 0.003361 | 0.0708 | 0.003933 | 0.0934 | 0.005189 |
| 1B2A3B | 0.0235 | 0.001306 | 0.0524 | 0.002911 | 0.0824 | 0.004578 | 0.0937 | 0.005206 |
| 1B2A3C | 0.0073 | 0.000406 | 0.0241 | 0.001339 | 0.0371 | 0.002061 | 0.0508 | 0.002822 |
| 1B2B3B | 0.0141 | 0.000783 | 0.046 | 0.002556 | 0.0638 | 0.003544 | 0.0899 | 0.004994 |
| 1B2B3C | 0.0124 | 0.000689 | 0.0209 | 0.001161 | 0.0459 | 0.00255 | 0.043 | 0.002389 |
| 1B2C3C | 0.006 | 0.000333 | 0.0284 | 0.001578 | 0.032 | 0.001778 | 0.0533 | 0.002961 |
| 1D2A3A | 0.0135 | 0.00075 | 0.029 | 0.001611 | 0.0335 | 0.001861 | 0.046 | 0.002556 |
| 1D2A3C | 0.0078 | 0.000433 | 0.0243 | 0.00135 | 0.0283 | 0.001572 | 0.0329 | 0.001828 |
| 1D2C3A | 0.0078 | 0.000433 | 0.023 | 0.001278 | 0.0265 | 0.001472 | 0.0369 | 0.00205 |
| 1G2A3C | 0.0156 | 0.000867 | 0.03 | 0.001667 | 0.086 | 0.004778 | 0.0877 | 0.004872 |

Figure 8

| Compound | H$_2$O:IL Ratio | | | |
|---|---|---|---|---|
| | Day 1 | Day 4 | Day 7 | Day 14 |
| 1B2A3A | 3.330481 | 11.64706 | 13.62995 | 17.98075 |
| 1B2A3B | 6.33603 | 14.128 | 22.21655 | 25.26323 |
| 1B2A3C | 2.421521 | 7.994337 | 12.30663 | 16.85113 |
| 1B2B3B | 3.722959 | 12.14582 | 16.84573 | 23.73717 |
| 1B2B3C | 5.472179 | 9.223269 | 20.25589 | 18.9761 |
| 1B2C3C | 1.758777 | 8.324875 | 9.380141 | 15.6238 |
| 1D2A3A | 8.423913 | 18.09581 | 20.90378 | 28.7037 |
| 1D2A3C | 5.270568 | 16.41985 | 19.1227 | 22.23099 |
| 1D2C3A | 5.086957 | 15 | 17.28261 | 24.06522 |
| 1G2A3C | 4.681104 | 9.002123 | 25.80609 | 26.31621 |

| Compound | Mass % H$_2$O | | | |
|---|---|---|---|---|
| | Day 1 | Day 4 | Day 7 | Day 14 |
| 1B2A3A | 15.61372 | 39.28571 | 43.09191 | 49.97325 |
| 1B2A3B | 23.08448 | 40.09181 | 51.27567 | 54.47674 |
| 1B2A3C | 8.138239 | 22.62911 | 31.04603 | 38.13814 |
| 1B2B3B | 14.53608 | 35.68658 | 43.49012 | 52.02546 |
| 1B2B3C | 16.29435 | 24.70449 | 41.87956 | 40.29991 |
| 1B2C3C | 5.888126 | 22.84795 | 25.01955 | 35.72386 |
| 1D2A3A | 32.84672 | 51.23675 | 54.82815 | 62.5 |
| 1D2A3C | 16.56051 | 38.20755 | 41.86391 | 45.56787 |
| 1D2C3A | 22.0339 | 45.45455 | 48.98336 | 57.2093 |
| 1G2A3C | 16.57811 | 27.64977 | 52.27964 | 52.76775 |

Figure 11

| Product | Amine | | | Sultone | | |
|---|---|---|---|---|---|---|
| | Name | Mass (g) | Moles | Name | Mass (g) | Moles |
| (sec-butyl ammonium propanesulfonate structure) | sec-butylamine | 6.32 | 0.0864 | propanesultone | 10.55 | 0.0864 |
| (hexyl ammonium propanesulfonate structure) | hexylamine | 8.38 | 0.0829 | propanesultone | 10.12 | 0.0829 |
| (isopropyl ammonium propanesulfonate structure) | isopropylamine | 4.90 | 0.0829 | propanesultone | 10.13 | 0.0829 |
| (ethanolammonium propanesulfonate structure) | ethanolamine | 4.97 | 0.0813 | propanesultone | 9.93 | 0.0813 |
| (2-ethylhexyl ammonium propanesulfonate structure) | 2-ethylhexylamine | 14.20 | 0.1099 | propanesultone | 13.42 | 0.1099 |
| (2-aminoheptane propanesulfonate structure) | 2-aminoheptane | 9.73 | 0.0844 | propanesultone | 10.31 | 0.0844 |
| (1,5-dimethylhexyl ammonium propanesulfonate structure) | 1,5-dimethylhexylamine | 10.25 | 0.0793 | propanesultone | 9.69 | 0.0793 |
| (sec-butyl ammonium butanesulfonate structure) | sec-butylamine | 2.69 | 0.0367 | 2,4-butanesultone | 5.00 | 0.0367 |
| (hexyl ammonium butanesulfonate structure) | hexylamine | 3.72 | 0.0367 | 2,4-butanesultone | 5.00 | 0.0367 |
| (isopropyl ammonium butanesulfonate structure) | isopropylamine | 2.17 | 0.0367 | 2,4-butanesultone | 5.00 | 0.0367 |

Figure 12

| Product | Amine Name | Mass (g) | Moles | Sultone Name | Mass (g) | Moles |
|---|---|---|---|---|---|---|
| HO-N(H₂)-CH₂CH₂CH(SO₃⁻)CH₃ | ethanolamine | 2.24 | 0.0367 | 2,4-butanesultone | 5.00 | 0.0367 |
| (2-ethylhexyl)-NH₂⁺-CH₂CH₂CH(SO₃⁻)CH₃ | 2-ethylhexylamine | 4.75 | 0.0367 | 2,4-butanesultone | 5.00 | 0.0367 |
| (2-heptyl)-NH₂⁺-CH₂CH₂CH(SO₃⁻)CH₃ | 2-aminoheptane | 4.23 | 0.0367 | 2,4-butanesultone | 5.00 | 0.0367 |
| (1,5-dimethylhexyl)-NH₂⁺-CH₂CH₂CH(SO₃⁻)CH₃ | 1,5-dimethylamine | 4.80 | 0.0372 | 2,4-butanesultone | 5.06 | 0.0372 |
| sec-butyl-NH₂⁺-(CH₂)₄-SO₃⁻ | sec-butylamine | 3.80 | 0.0519 | 1,4-butanesultone | 7.07 | 0.0519 |
| hexyl-NH₂⁺-(CH₂)₄-SO₃⁻ | hexylamine | 2.25 | 0.0518 | 1,4-butanesultone | 7.06 | 0.0518 |
| isopropyl-NH₂⁺-(CH₂)₄-SO₃⁻ | isopropylamine | 3.06 | 0.0517 | 1,4-butanesultone | 7.04 | 0.0517 |
| HO-CH₂CH₂-NH₂⁺-(CH₂)₄-SO₃⁻ | ethanolamine | 3.14 | 0.0515 | 1,4-butanesultone | 7.01 | 0.0515 |

| Product | Amine Name | Mass (g) | Moles | Sultone Name | Mass (g) | Moles |
|---|---|---|---|---|---|---|
| (2-ethylhexyl)-NH₂⁺-(CH₂)₄-SO₃⁻ | 2-ethylhexylamine | 6.69 | 0.0518 | 1,4-butanesultone | 7.05 | 0.0518 |
| (2-heptyl)-NH₂⁺-(CH₂)₄-SO₃⁻ | 2-aminoheptane | 5.61 | 0.0487 | 1,4-butanesultone | 6.63 | 0.0487 |
| (1,5-dimethylhexyl)-NH₂⁺-(CH₂)₄-SO₃⁻ | 1,5-dimethylamine | 6.68 | 0.0517 | 1,4-butanesultone | 7.04 | 0.0517 |

Figure 13

| Product - Propanesultone | Zwitterion Mass (g) | Moles | Ammonium Salt Name | Moles Salt | Mass Soln | Solvent | Titer | Yield (g) |
|---|---|---|---|---|---|---|---|---|
| [structure: sec-butylamino propanesulfonate tetramethylammonium] | 0.64 | 0.0033 | Tetramethyl ammonium hydroxide | 0.0033 | 1.23 | water | 24.2 | 0.86 |
| [structure: hexylamino propanesulfonate tetramethylammonium] | 1.00 | 0.0045 | Tetramethyl ammonium hydroxide | 0.0045 | 1.69 | methanol | 24.2 | 1.33 |
| [structure: isopropylamino propanesulfonate tetramethylammonium] | 1.15 | 0.0064 | Tetramethyl ammonium hydroxide | 0.0064 | 2.39 | methanol | 24.2 | 1.63 |
| [structure: HO-ethylamino propanesulfonate tetramethylammonium] | 0.83 | 0.0045 | Tetramethyl ammonium hydroxide | 0.0045 | 1.65 | water | 25.06 | 1.15 |
| [structure: 2-ethylhexylamino propanesulfonate tetramethylammonium] | 0.56 | 0.0022 | Tetramethyl ammonium hydroxide | 0.0022 | 0.84 | methanol | 24.2 | 0.73 |
| [structure: sec-octylamino propanesulfonate tetramethylammonium] | 0.74 | 0.0031 | Tetramethyl ammonium hydroxide | 0.0031 | 1.14 | water | 25.06 | 0.96 |
| [structure: branched alkylamino propanesulfonate tetramethylammonium] | 3.50 | 0.0139 | Tetramethyl ammonium hydroxide | 0.0139 | 5.24 | methanol | 24.2 | 4.51 |

Figure 14

| Product - Propanesultone | Zwitterion | | | Ammonium Salt | | | | |
|---|---|---|---|---|---|---|---|---|
| | Mass (g) | Moles | Name | Moles Salt | Mass Soln | Solvent | Titer | Yield (g) |
| 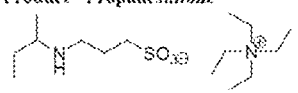 | 2.26 | 0.0116 | Tetraethyl ammonium hydroxide | 0.0116 | 4.80 | water | 35.5 | 3.76 |
| 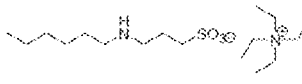 | 1.00 | 0.0045 | Tetraethyl ammonium hydroxide | 0.0045 | 1.86 | water | 35.5 | 1.59 |
| 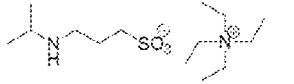 | 0.41 | 0.0023 | Tetraethyl ammonium hydroxide | 0.0023 | 0.94 | water | 35.5 | 0.71 |
| 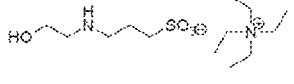 | 0.79 | 0.0043 | Tetraethyl ammonium hydroxide | 0.0043 | 1.79 | water | 35.5 | 1.34 |
| 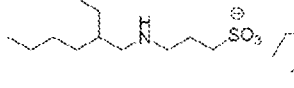 | 0.58 | 0.0023 | Tetraethyl ammonium hydroxide | 0.0023 | 0.96 | water | 35.5 | 0.88 |
| 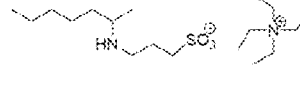 | 1.02 | 0.0043 | Tetraethyl ammonium hydroxide | 0.0043 | 1.79 | water | 35.5 | 1.58 |
| 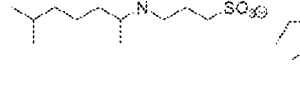 | 3.01 | 0.0120 | Tetraethyl ammonium hydroxide | 0.0120 | 4.98 | water | 35.5 | 4.57 |

Figure 15

| Product - Propanesultone | Zwitterion | | | Ammonium Salt | | | | Yield (g) |
|---|---|---|---|---|---|---|---|---|
| | Mass (g) | Moles | Name | Moles Salt | Mass Soln | Solvent | Titer | |
| 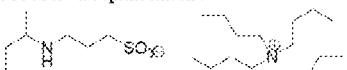 | 2.28 | 0.0117 | Tetrabutyl ammonium hydroxide | 0.0117 | 7.57 | water | 40.0 | 5.11 |
| 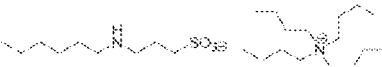 | 1.00 | 0.0045 | Tetrabutyl ammonium hydroxide | 0.0045 | 2.90 | water | 40.0 | 2.09 |
| 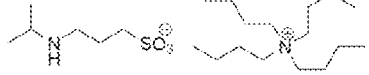 | 0.48 | 0.0027 | Tetrabutyl ammonium hydroxide | 0.0027 | 1.72 | water | 40.0 | 1.14 |
| 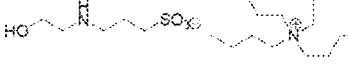 | 0.93 | 0.0051 | Tetrabutyl ammonium hydroxide | 0.0051 | 5.08mL | methanol | 1.0M | 2.17 |
| 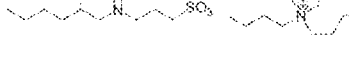 | 0.56 | 0.0022 | Tetrabutyl ammonium hydroxide | 0.0022 | 1.45 | water | 40.0 | 1.08 |
| 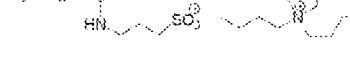 | 0.92 | 0.0039 | Tetrabutyl ammonium hydroxide | 0.0039 | 3.88mL | methanol | 1.0M | 1.87 |
|  | 1.50 | 0.0060 | Tetrabutyl ammonium hydroxide | 0.0060 | 3.87 | water | 40.0 | 2.96 |

Figure 16

| Product - 2,4-butanesultone | Zwitterion Mass (g) | Moles | Ammonium Salt Name | Moles Salt | Mass Solution (g) | Solvent | Titer | Yield (g) |
|---|---|---|---|---|---|---|---|---|
| | 0.62 | 0.0030 | Tetramethylammonium hydroxide | 0.0030 | 1.12 | methanol | 24.2 | 0.85 |
| | 0.56 | 0.0024 | Tetramethyl ammonium hydroxide | 0.0024 | 0.77 | water | 25.06 | 0.75 |
| | 0.78 | 0.004 | Tetramethyl ammonium hydroxide | 0.004 | 1.5 | methanol | 24.3 | 1.07 |
| | 0.59 | 0.0030 | Tetramethyl ammonium hydroxide | 0.0030 | 1.13 | methanol | 24.3 | 0.81 |
| | 0.77 | 0.0029 | Tetramethyl ammonium hydroxide | 0.0029 | 1.07 | water | 25.06 | 0.98 |
| | 0.51 | 0.0020 | Tetramethyl ammonium hydroxide | 0.0020 | 0.74 | water | 25.06 | 0.65 |
| | 0.75 | 0.0028 | Tetramethyl ammonium hydroxide | 0.0028 | 1.07 | methanol | 24.2 | 0.95 |
| | 0.84 | 0.0031 | Tetraethyl ammonium hydroxide | 0.0031 | 1.27 | water | 35.3 | 1.05 |
| | 0.56 | 0.0024 | Tetraethyl ammonium hydroxide | 0.0024 | 0.98 | water | 35.3 | 0.88 |

Figure 17

The figure shows a table with structural drawings of zwitterion products from 2,4-butanesultone reactions, along with the following columns: Product - 2,4-butanesultone (structure), Zwitterion Mass (g), Moles, Ammonium Salt Name, Moles Salt, Mass Solution (g), Solvent, Titer, Yield (g).

| Zwitterion Mass (g) | Moles | Name | Moles Salt | Mass Solution (g) | Solvent | Titer | Yield (g) |
|---|---|---|---|---|---|---|---|
| 0.83 | 0.0042 | Tetraethyl ammonium hydroxide | 0.0042 | 1.74 | water | 35.5 | 1.36 |
| 0.63 | 0.0032 | Tetraethyl ammonium hydroxide | 0.0032 | 1.33 | water | 35.5 | 1.04 |
| 0.73 | 0.0028 | Tetraethyl ammonium hydroxide | 0.0028 | 1.17 | water | 35.5 | 1.11 |
| 0.54 | 0.0022 | Tetraethyl ammonium hydroxide | 0.0022 | 0.89 | water | 35.5 | 0.83 |
| 0.72 | 0.0029 | Tetraethyl ammonium hydroxide | 0.0029 | 1.21 | water | 35.5 | 1.14 |
| 0.63 | 0.0030 | Tetrabutyl ammonium hydroxide | 0.0030 | 2.97 mL | methanol | 1.0 M | 1.35 |
| 0.47 | 0.0020 | Tetrabutyl ammonium hydroxide | 0.0020 | 1.98 mL | methanol | 1.0 M | 0.98 |
| 0.86 | 0.0044 | Tetrabutyl ammonium hydroxide | 0.0044 | 2.26 | water | 40.0 | 1.92 |

Figure 18

| Product - 1,4-butanesultone | Zwitterion Mass (g) | Moles | Name | Ammonium Salt Moles Salt | Mass Solution (g) | Solvent | Titer | Yield (g) |
|---|---|---|---|---|---|---|---|---|
| [structure] | 0.58 | 0.0029 | Tetrabutyl ammonium hydroxide | 0.0029 | 2.94mL | methanol | 1.0M | 1.27 |
| [structure] | 0.74 | 0.0028 | Tetrabutyl ammonium hydroxide | 0.0028 | 2.79mL | methanol | 1.0M | 1.40 |
| [structure] | 0.54 | 0.0022 | Tetrabutyl ammonium hydroxide | 0.0022 | 2.13mL | methanol | 1.0M | 1.08 |
| [structure] | 0.78 | 0.0029 | Tetrabutyl ammonium hydroxide | 0.0029 | 2.87mL | methanol | 1.0M | 1.47 |

| Product - 1,4-butanesultone | Zwitterion Mass (g) | Moles | Name | Ammonium Salt Moles Salt | Mass Solution (g) | Solvent | Titer | Yield (g) |
|---|---|---|---|---|---|---|---|---|
| [structure] | 0.85 | 0.0033 | Tetrabutyl ammonium hydroxide | 0.0033 | 3.30mL | methanol | 1.0M | 1.45 |
| [structure] | 0.46 | 0.0017 | Tetrabutyl ammonium hydroxide | 0.0017 | 1.74mL | methanol | 1.0M | 0.86 |
| [structure] | 0.73 | 0.0029 | Tetrabutyl ammonium hydroxide | 0.0029 | 2.90mL | methanol | 1.0M | 1.43 |
| [structure] | 0.91 | 0.0034 | Tetrabutyl ammonium hydroxide | 0.0034 | 3.43mL | methanol | 1.0M | 1.72 |

Figure 19

| Product - 1,4-butanesultone | Zwitterion Mass (g) | Moles | Name | Ammonium Salt Moles Salt | Mass Solution (g) | Solvent | Filter | Yield (g) |
|---|---|---|---|---|---|---|---|---|
| (structure) | 0.67 | 0.0031 | Tetramethyl ammonium hydroxide | 0.0031 | 1.13 | water | 25.00 | 0.88 |
| (structure) | 0.63 | 0.0026 | Tetramethyl ammonium hydroxide | 0.0026 | 0.94 | water | 25.00 | 0.81 |
| (structure) | 0.77 | 0.0039 | Tetramethyl ammonium hydroxide | 0.0039 | 1.44 | water | 25.00 | 1.06 |
| (structure) | 0.39 | 0.003 | Tetramethyl ammonium hydroxide | 0.003 | 1.09 | water | 25.00 | 0.81 |
| (structure) | 0.43 | 0.0016 | Tetramethyl ammonium hydroxide | 0.0016 | 0.59 | water | 25.00 | 0.54 |
| (structure) | 0.71 | 0.0028 | Tetramethyl ammonium hydroxide | 0.0028 | 1.03 | water | 25.00 | 0.91 |
| (structure) | 0.84 | 0.0032 | Tetramethyl ammonium hydroxide | 0.0032 | 1.17 | water | 25.00 | 1.08 |
| (structure) | 0.82 | 0.0032 | Tetramethyl ammonium hydroxide | 0.0032 | 1.17 | water | 37.5 | 1.08 |
| (structure) | 1.06 | 0.0045 | Tetramethyl ammonium hydroxide | 0.0045 | 1.66 | water | 37.5 | 1.05 |

Figure 20

| Product - 1,4-butanesultone | Zwitterion Mass (g) | Moles | Name | Ammonium Salt Moles Salt | Mass Solution (g) | Solvent | Titer | Yield (g) |
|---|---|---|---|---|---|---|---|---|
| [structure] | 0.98 | 0.0030 | Tetraethyl ammonium hydroxide | 0.0030 | 2.09 | water | 35.5 | 1.62 |
| [structure] | 0.62 | 0.0031 | Tetraethyl ammonium hydroxide | 0.0031 | 1.30 | water | 35.5 | 1.04 |
| [structure] | 0.43 | 0.0016 | Tetraethyl ammonium hydroxide | 0.0016 | 0.67 | water | 35.5 | 0.63 |
| [structure] | 0.75 | 0.003 | Tetraethyl ammonium hydroxide | 0.003 | 1.24 | water | 35.5 | 1.14 |
| [structure] | 0.82 | 0.0035 | Tetraethyl ammonium hydroxide | 0.0035 | 1.44 | water | 35.5 | 1.38 |
| [structure] | 0.84 | 0.003 | Tetrabutyl ammonium hydroxide | 0.003 | 3.06 mL | methanol | 1.0 M | 1.55 |
| [structure] | 0.62 | 0.0026 | Tetrabutyl ammonium hydroxide | 0.0026 | 2.61 mL | methanol | 1.0 M | 1.24 |
| [structure] | 0.85 | 0.0044 | Tetrabutyl ammonium hydroxide | 0.0044 | 4.36 mL | methanol | 1.0 M | 1.62 |

CARBON DIOXIDE SCRUBBING USING IONIC MATERIALS

RELATED APPLICATIONS

This application is a divisional of U.S. patent application No. 12/594,442, filed Jan. 12, 2010, now U.S. Pat. No. 8,536,371, which is the U.S. National Stage of International Patent Application No. PCT/US2008/059099, filed Apr. 2, 2008, which claims the benefit of U.S. Provisional Patent Application Ser. No. 60/909,538, filed Apr. 2, 2007; and U.S. Provisional Patent Application Ser. No. 60/990,128, filed Nov. 26, 2007; all of which are hereby incorporated by reference in their entireties.

BACKGROUND OF THE INVENTION

Carbon dioxide is a chemical chimera. Essential to life by virtue of its role as the carbon supplier in photosynthesis, it has also come to be regarded as an environmental threat due to its contributions to global warming. Likewise, while certain recent work has constructively harnessed $CO_2$ to form novel soft materials, other current research focuses on the synthesis of new materials explicitly for achieving $CO_2$ removal when its presence constitutes a nuisance.

The reversible capture of $CO_2$ is a process of importance in applications ranging from respiration devices to natural gas sweetening (Stewart, C.; Hessami, M.-A. *Energy Conv. Mgmt.*, 2005, 46, 403; Harrison, D. P.; Silaban, A. *Chem. Eng. Comm.* 1995, 137, 177). For example, the reversible capture of $CO_2$ is a prominent feature of schemes for the mitigation of causative agents in global warming. Already important in the purification of natural gas and in breathing-air recirculation systems, $CO_2$ capture is achieved on large scales by passing a contaminated gas through an aqueous amine solution, with which the entrained $CO_2$ reacts (Kohl, A.; Nielsen, R. *Gas Purification*, 5th ed., Gulf: Houston, 1997; Chapters 1, 2, and 14). Unfortunately, the process is frustrated by the volatility of the dissolved amines, which are gradually lost into the gas stream. Accordingly, if reactive capture is to be an element of future $CO_2$ management technologies, there is a pressing need to develop systems in which the scavenger is both affordable and non-volatile.

One of the most promising new categories of materials for use in $CO_2$ removal is ionic liquids (ILs). At higher pressures, $CO_2$ has a greater innate solubility in many classical ILs than do other gases, making physical solvation a potential method of removal. At lower pressures, reactive gas capture by amine-functionalized task-specific ionic liquids (TSILs) is promising. Using these functional salts, it is possible to capture $CO_2$ in a fashion akin to commercial scrubbing amines while avoiding backpressure from the amine and the slow loss of the amine into the treated gas stream (Bates, E. D. et al. *J. Am. Chem. Soc.* 2002, 124, 4194). Since ionic liquids (ILs) typically lack a detectable vapor pressure, they are conceptually ideal materials for $CO_2$ capture technology (Bates, E. D. et al. *J. Am. Chem. Soc.* 2002, 124, 4194; Zhang, J. et al. *Chem. Eur. J.* 2006, 12, 4021; Huang, J. et al. *Chem. Comm.* 2006, 4027; Anthony, J. L. et al. *Int. J. Envir. Tech. Mgmt.* 2004, 4, 105). However, the scales involved in industrial capture applications require large amounts of the reactive agents. Moreover, some amine-functionalized TSILs are relatively costly and/or tedious to prepare and purify. Further, these TSILs have or potentially have problems with long-term stability.

Accordingly, it is important to find new $CO_2$-reactive TSILs and related soft ionic materials, especially by co-opting commercially available commodity chemicals as starting materials, and assembling them in quick, high-yielding and atom-efficient reactions. Furthermore, since the ultimate goal is the development of property-tunable ionic materials for large-scale $CO_2$ scavenging, it is vital to identify alternatives which can be made using a procedure that is uncomplicated, economically attractive, and capable of quickly producing a large number of materials for screening purposes. Specifically, an approach which embodies attributes of the Kolb, Finn and Sharpless "click" concept (rapid, modular, employing commodity chemicals, highly atom efficient, using minimal and/or relatively benign solvents, and giving high yields of products useable with little or no purification) is desired (Kolb, H. C.; Finn, M. G.; Sharpless, K. B. *Angew. Chem. Int. Ed.* 2001, 40, 2004).

SUMMARY OF THE INVENTION

One aspect of the present invention relates to amine-functionalized task-specific ionic liquids (TSILs). In certain embodiments, the ionic liquids of the invention comprise 1,3-diamines, beta-hydroxy amines, aryl amines or tertiary amines. The TSILs may be used for gas capture, capitalizing on their non-volatile nature. In certain embodiments, the captured gas is selected from the group consisting of $CO_2$, $SO_2$, $CS_2$, and $NO_2$. In certain embodiments, the captured gas is $CO_2$.

Another aspect of the present invention relates to a library of $CO_2$-philic salts, which library facilitates reactive gas separation. In certain embodiments, the $CO_2$-philic salts are $CO_2$-reactive TSILs. Remarkably, in certain embodiments, the $CO_2$-philic salts are resinous or plastic in nature.

In certain embodiments, the compounds of the present invention are prepared from commodity chemicals, including but not limited to primary amines, secondary amines, diamines, sultones, epoxides, aryl amines and quaternary ammonium hydroxides.

In certain embodiments, preparing a compound of the invention comprises one or more high-yielding, atom-efficient "click" reactions that produce water as the sole byproduct (Kolb, H. C.; Finn, M. G.; Sharpless, K. B. *Angew. Chem. Int. Ed.* 2001, 40, 2004). In certain embodiments, the nucleophile of this reaction consists of an uncharged Lewis base; i.e., a compound that contains a lone pair of electrons but has no net charge. In certain embodiments, the nucleophile is a primary, secondary, tertiary amine, or diamine In certain embodiments, one synthetic step involves the reaction between an amine and a sultone. In certain embodiments, one synthetic step involves the reaction between an amine, or a zwitterion, and an epoxide. In certain embodiments, in one synthetic step a zwitterion intermediate undergoes simultaneous deprotonation and ion exchange by reaction of the intermediate with an ammonium hydroxide salt or other hydroxide base.

In certain embodiments, a salt of the present invention is hydrophilic. In certain embodiments, a salt of the present invention is an ionic liquid. In certain embodiments, a salt of the present invention is a plastic or resin. In certain embodiments, a salt of the present invention is a solid.

Another aspect of this invention is a method for the reversible uptake of a gas by a salt of the present invention. In certain embodiments, the gas is $CO_2$. The uptake of $CO_2$ by any of the salts of the present invention, which occurs even when the salts are exposed to air, has been demonstrated in a variety of fashions. In certain embodiments, after $CO_2$ exposure, qualitative evidence of $CO_2$ uptake is manifest by an increase in viscosity, solidification, or the development of a frosted appearance by a resinous or plastic salt of the present invention.

BRIEF DESCRIPTION OF THE FIGURES

FIG. 2 depicts [A] a synthetic scheme for selected CO$_2$-philic materials; and [B] images showing [1B2A3A] "sliced" and removed in strips from the reaction vessel in which it was prepared as a transparent, somewhat tacky, moldable film (using a solvent evaporation approach it can be applied to the coils of a condenser which is then fitted with gas adapters at each end to create a simple, recyclable, pass-through CO$_2$ absorber).

FIGS. 4-6 tabulate CO$_2$ capture data based upon comparative IR spectra before and after exposure (the appearance of a peak between 1619-1654 cm$^{-1}$ is diagnostic for the sequestration of CO$_2$ as carbamate). The observance of small peaks (IR) for carbamate even before deliberate exposure to a CO$_2$ stream apparently results from CO$_2$ absorption from the air. All compounds were azeotropically dried with benzene and held under vacuum for at least 12 hours. The compounds that are resinous or plastic in nature (indicated in bold print) were also examined for CO$_2$ capture after being allowed to saturate with water vapor in a sealed container.

FIGS. 7-8 tabulate the mass changes (at intervals of 1, 4, 7 and 14 days) of samples of various salts of the invention stored in a sealed container above a water reservoir.

FIGS. 11-20 depict experimental data for the syntheses of various zwitterions and the syntheses of various TSILs derived from such zwitterions.

DETAILED DESCRIPTION OF THE INVENTION

Figure 1:
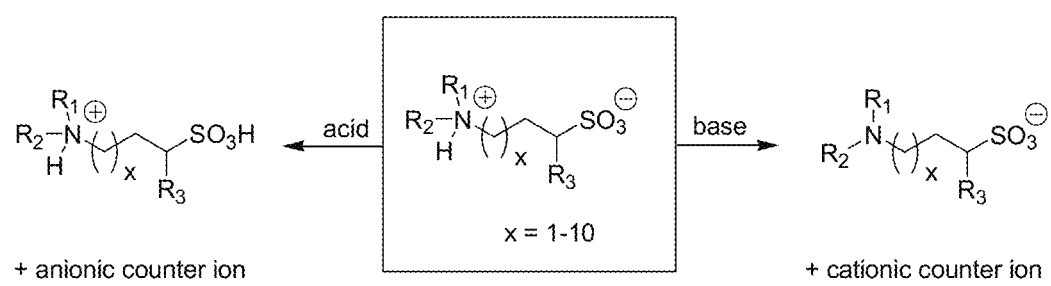
FIG. 1 depicts a generic synthetic scheme for the production of certain cationic and anionic $CO_2$-philic materials from a zwitterionic intermediate.
Figure 3:
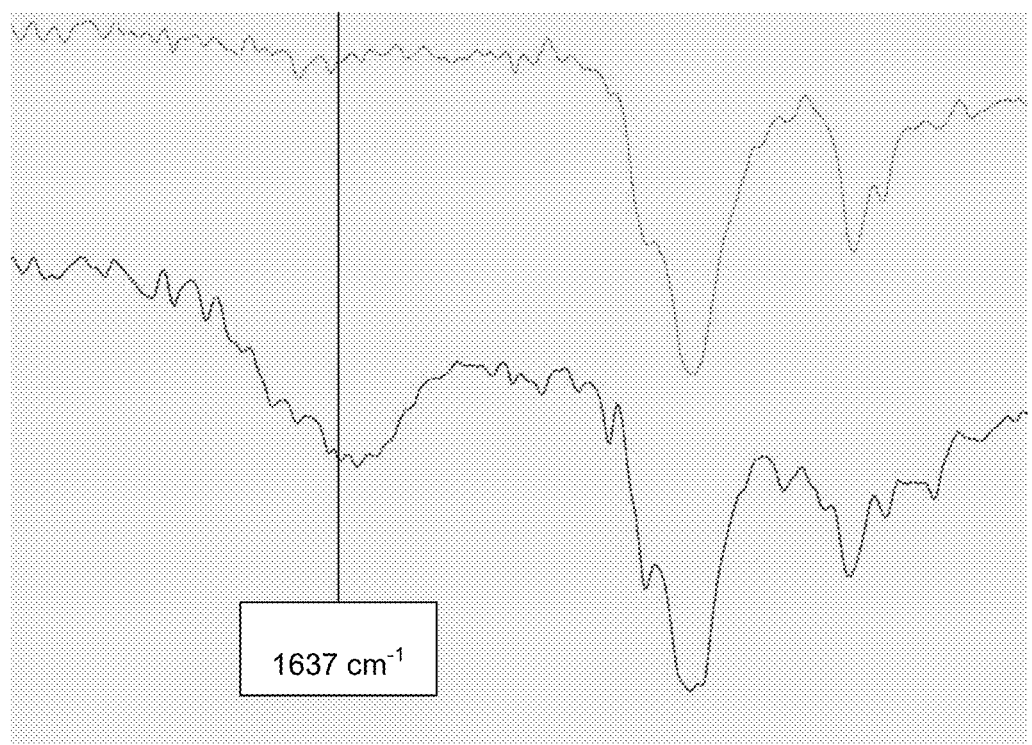
FIG. 3 depicts the carbonyl region of FTIR spectra of [1B2A3C] before (upper) and after (lower) CO$_2$ exposure.
Figure 9:
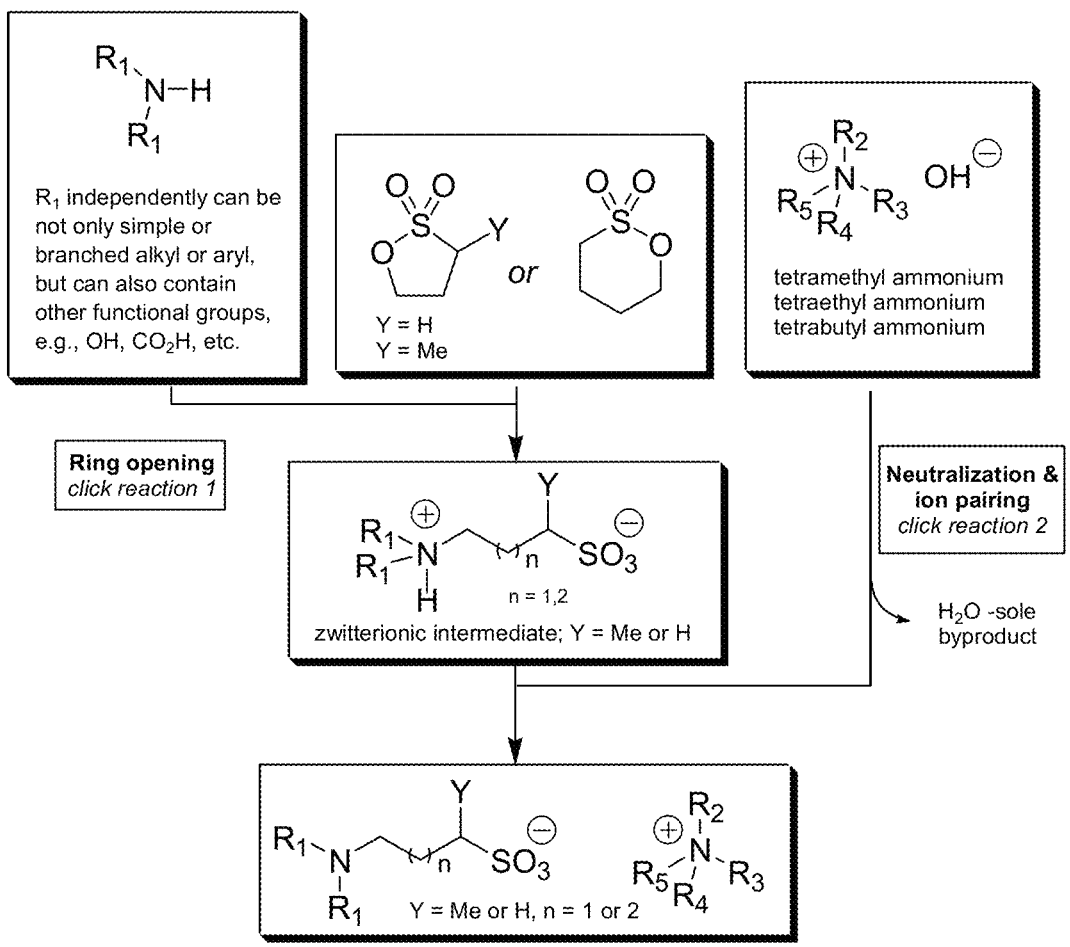
FIGS. 9-10 depict generic synthetic schemes for certain CO$_2$-philic materials of the present invention which are prepared via a zwitterionic intermediate.
Figure 10:
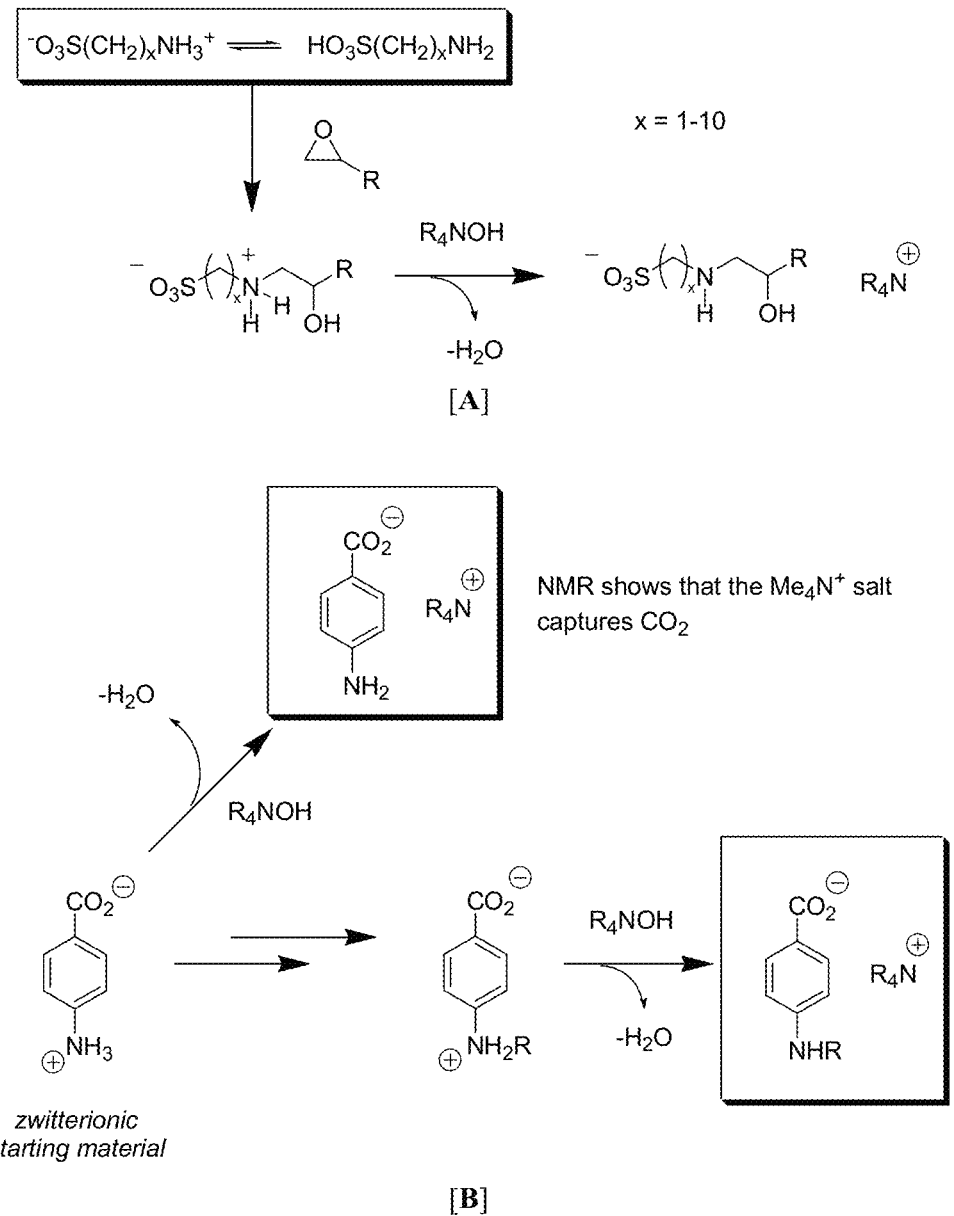

One aspect of the present invention relates to amine-functionalized task-specific ionic liquids (TSILs) for gas capture, which capitalize on the non-volatile nature of these salts (see Lee, S.-G. *Chem. Commun.* 2006, 1049; Davis, J. H., Jr. *Chemistry Letters* 2004, 33, 1072). In certain embodiments, the amine-functionalized task-specific ionic liquids comprise diamines, beta-hydroxy amines, aryl amines and/or tertiary amines. Zhang has shown that amine-functionalized TSILs need not be in a bulk liquid form to capture CO$_2$, but could also do so when supported on a solid (Zhang, J. et al. *Chem. Eur. J.* 2006, 12, 4021). Together, these findings support the proposition that amine-functionalized salts in various forms are promising gas-scavenging materials. In certain embodiments, the gas is selected from the group consisting of CO$_2$, SO$_2$, CS$_2$, and NO$_2$. In certain embodiments, the gas is CO$_2$.

Another aspect of the present invention relates to CO$_2$-philic salts or a library of them, which library is the first created to facilitate a reactive gas separation. In certain embodiments, the CO$_2$-philic salts are CO$_2$-reactive TSILs.

Remarkably, in certain embodiments, the CO$_2$-philic salts are resinous or plastic in nature. Although the low molecular mass organogelation (LMOG) or water-induced formation of IL gels is known (Henderson, D., Holovko, M.; Trokhymchuk, A., Eds. *Ionic Soft Matter: Modern Trends in Theory and Applications*; NATO Science Series II, 206; Springer: Dordrecht, 2005), the reactions of CO$_2$ with amine-modified polymers (Henderson, D., Holovko, M.; Trokhymchuk, A., Eds. *Ionic Soft Matter: Modern Trends in Theory and Applications*; NATO Science Series II, 206; Springer: Dordrecht, 2005), and the CO$_2$-induced formation of soft matter (Ohno, H., Ed. *Electrochemical Aspects of Ionic Liquids*; Wiley: Hoboken, 2005, 323-336; Liu, Y. et al. Science, 2006, 313, 958; Rudkevich, D. M.; Xu, H. *Chem. Commun.* 2005, 2651; George, M.; Weiss, R. G. *J. Am. Chem. Soc.* 2001, 123, 10393), the soft ionic phases of the present invention are remarkable materials for CO$_2$ capture. The physical states of these soft ionic phases render them easy to apply to almost any solid surface on which they form durable deposits, which surfaces include glass, plastics, textiles and metals.

In certain embodiments, the compounds of the present invention are made from commodity chemicals. In certain embodiments, these chemicals include primary amines, secondary amines, diamines, sultones, epoxides, and quaternary ammonium hydroxides. In certain embodiments, their modular nature lends them to combinatorial assembly via an inexpensive process.

In certain embodiments, the process comprises one or more high-yielding, atom-efficient "click" reactions that produce water as the sole byproduct (Kolb, H. C.; Finn, M. G.; Sharpless, K. B. *Angew. Chem. Int. Ed.* 2001, 40, 2004). Remarkably, these reactions require minimal amounts of inexpensive and benign solvents, are frequently rapid, and usually require no heating or cooling.

In certain embodiments, the materials produced in the present invention are serviceable for CO$_2$ capture without purification, which is an enormous advantage for any material being developed for large-scale use.

In certain embodiments, in the context of their function as TSIL components, the products of the ring opening have two key features. A key feature is the creation of a permanent anionic charge in the form of an alkane sulfonate group. This anion type is charge-diffuse and consequently poorly basic and poorly nucleophilic, both desirable attributes. Another key feature is the covalent tether between the anion and the amine group that is formed in the reaction.

In certain embodiments, the salts of the present invention are hydrophilic.

In certain embodiments, the salts are ionic liquids.

In certain embodiments, the salts are plastic or resin.

In certain embodiments, the salts are solid.

In certain embodiments, water is removed from the salts by azeotropic drying and storage under vacuum over solid P$_2$O$_5$.

In certain embodiments, water levels as low as about 10%.

In certain embodiments, water levels as low as about 4%. In certain embodiments, water levels as low as about 3%.

In certain embodiments, water levels as low as about 2%.

In certain embodiments, the materials that are plastics and resins have varying capacities to absorb water while retaining their structural integrity.

In certain embodiments, these materials resist deliquescence for days when sealed in an atmosphere of water-saturated air.

Another aspect of this invention is the reversible uptake of a gas by a material of the present invention.

In certain embodiments, the gas is CO$_2$. The uptake of CO$_2$ by any of the salts of the present invention, which occurs even when the salts are left open to air, can be demonstrated in a variety of fashions.

In certain embodiments, after CO$_2$ exposure, qualitative evidence of CO$_2$ uptake may be manifest in a visible increase in the viscosities or occasional solidification of those that are liquids; and the frosted appearance of those that are resins.

In certain embodiments, TSIL samples charged with indicator dye change from sapphire to bright green on exposure to the gas (see MacFarlane, D. R. et al. *Chem. Commun.* 2006, 1905). In certain embodiments, the dye-charged resins also respond in this fashion, suggesting a potential for their development as apply-anywhere colorimetric CO$_2$ sensors.

Unambiguous evidence of CO$_2$ binding is provided by FTIR, $^{13}$C-NMR, and ESI-MS. For example, in certain embodiments marked changes in the $^{13}$C spectrum of compounds of the invention when treated with a stream of CO$_2$ may be observed; including the appearance of a strong new signal at about 160 ppm. This new signal is consistent with the CO$_2$-supplied carbon atom of a newly formed carbamate (or, possibly, carbamic acid) group within the anion. In addition, the appearance of a peak between 1619-1654 cm$^{-1}$ in the FTIR is diagnostic for the sequestration of $CO_2$ as carbamate (see Pretsch et al. *Tables of Spectral Data for Structural Determination of Organic Compounds*, 2d ed.; Springer: Berlin, 1989; Silverstein et al. *Spectrometric Identification of Organic Compounds*, 5th ed.; Wiley: New York, 1991; Bates, E. D. et al. *J. Am. Chem. Soc.* 2002, 124, 4194; Zhang, J. et al. *Chem. Eur. J.* 2006, 12, 4021; Liu, Y. et al. Science, 2006, 313, 958; Rudkevich, D. M.; Xu, H. *Chem. Commun.* 2005, 2651; George, M.; Weiss, R. G. *J. Am. Chem. Soc.* 2001, 123, 10393). Further, negative-mode ESI-MS may provide additional evidence for the covalent incorporation of $CO_2$ into the anion structure. Further, if the intensity of peaks from the $CO_2$-containing ions diminishes with residence time in the mass spectrometer, this would provide further verification of the reversibility of the binding.

In certain embodiments, one synthetic step involves the reaction between an amine or a phosphine and a sultone. In certain embodiments, the sultone is 1,3-propanesultone. In certain embodiments, the sultone is 1,4-butane sultone. In certain embodiments, the sultone is represented by:

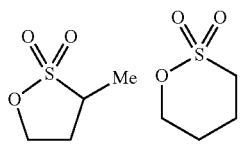

In certain embodiments, the sultone and amine or phosphine are combined to produce a zwitterion intermediate.

In certain embodiments, in one synthetic step the zwitterion intermediate undergoes simultaneous deprotonation and ion exchange by reaction of the intermediate with an ammonium hydroxide or other base. In other embodiments, the zwitterion intermediate undergoes protonation by an acid. See FIG. 1.

In certain embodiments, one synthetic step involves the reaction between an amine and a sultone. In certain embodiments, the amine is a primary, secondary, or tertiary amine. In certain embodiments, the reaction between the amine and sultone produces a zwitterion represented by:

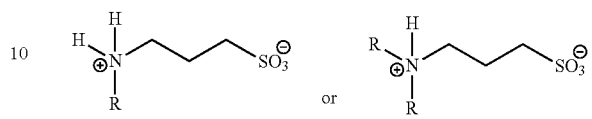

In certain embodiments, one synthetic step involves the reaction between a phosphine and a sultone. In certain embodiments, the phosphine has the formula $RPH_2$ or $R_2PH$. In certain embodiments, the reaction between the phosphine and sultone produces a zwitterion represented by:

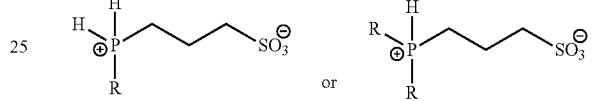

In certain embodiments, the anion in the compounds of the present invention has an impact on the properties of the final products. In certain embodiments, the cation in the compounds of the present invention has an impact on the properties of the final products.

In certain embodiments, the resulting intermediates and/or products are dried under vacuum.

In certain embodiments, selected synthetic steps are represented by the following schemes (reactions with primary amines, secondary amines or diamines):

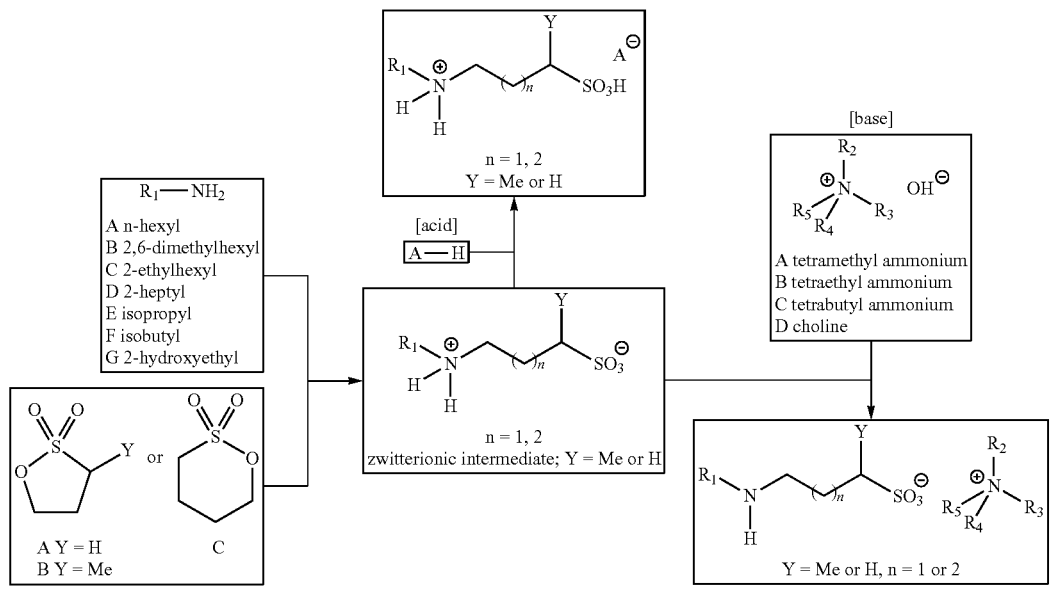

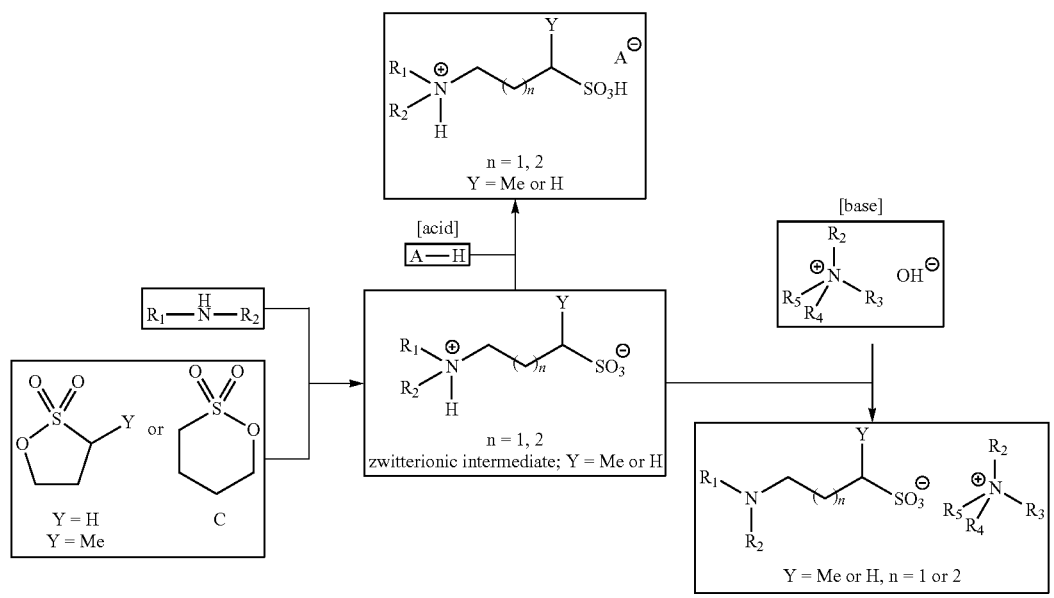
In certain embodiments, the zwiterionic intermediate can be reacted with an epoxide, as shown the schemes below. In certain embodiments, selected synthetic steps are represented by the following scheme:
A variety of zwitterionic intermediates can be used; for example, selected synthetic steps are represented by the following scheme:
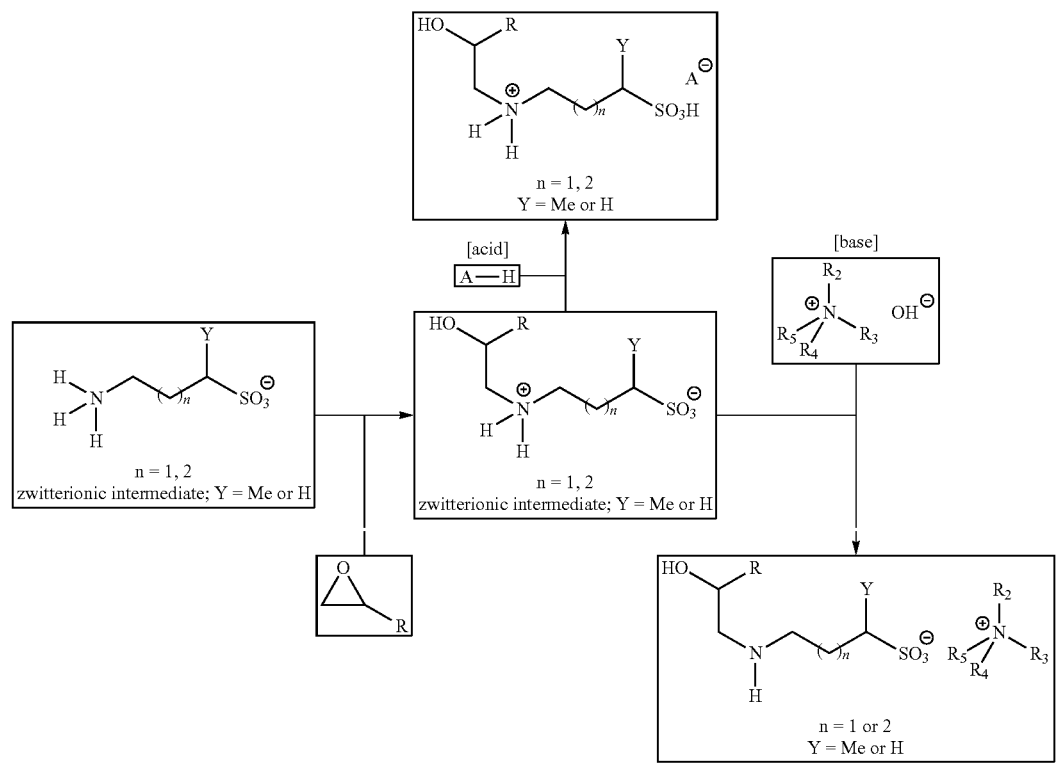

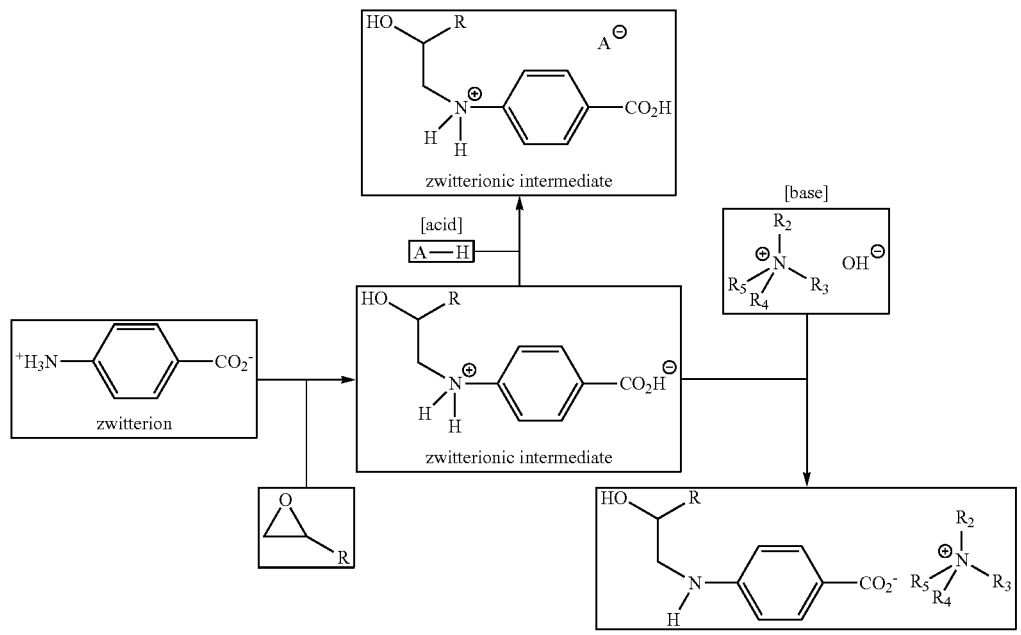

While many of the above examples have shown ammonium hydroxide salts, as the base, reacting with the zwiterionic intermediates, one may also use a phosphonium cation, a heterocyclic (e.g., imidazolium or pyridinium) cation, or in certain circumstances an alkali metal cation or an alkaline earth metal cation as the counterion. In certain embodiments, the cations can be metal cations, such as Na, K, Ca, Ba, etc.

While the selected synthetic routes described above have all suggested reacting hydroxide salts of various cations with the zwitterions, other synthetic approaches can be envisioned as well, such as zwitterion deprotonation with strong bases like NaH or BuLi, followed by an ion metathesis step to exchange the Na or Li for a different cation.

In certain embodiments, the anion in the compounds of the present invention is a homotaurine derivatives related to Zwittergent®-type detergents. Aqueous solutions of taurine/homotaurine capture $CO_2$ (see Wolfram, A. et al., DE 1071674). However, where the latter incorporate quaternary nitrogen centers arising from tertiary amine induced sultone ring-opening, the use of primary amines in certain embodiments of the present invention gives rise instead to secondary amine substituents. Interestingly, the presence of both a lone pair and a hydrogen atom on the nitrogen of the final anion are sometimes features for the capture of $CO_2$ as a carbamate; accepted as a key mechanism by which scrubbing amines function (Kohl, A.; Nielsen, R. *Gas Purification*, 5th ed.; Gulf: Houston, 1997; Chapters 1, 2, and 14).

Remarkably, in certain embodiments, the amine-provided alkyl group has a notable impact on the properties of the final products.

In certain embodiments, anions derived from [1A], [1B], [1C], and [1D] are more apt to form the resinous or plastic materials (see FIG. 2A).

DEFINITIONS. For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "ionic liquid" or "IL" as used herein means an organic salt or hydrate thereof with a melting point less than about 150° C. In a preferred embodiment, the ionic liquid has a melting point of less than about 100° C. In a preferred embodiment, the ionic liquid has a melting point of less than about 50° C. In a preferred embodiment, the ionic liquid has a melting point of less than about room temperature. The ionic liquids of the present invention may comprise one or more compounds. Thus, the ionic liquid may be a pure compound or may be a mixture of compounds. Each compound comprises an anion or a mixture of anions; and a cation or a mixture of cations.

The term "Lewis base" as used herein is a substance which acts as an electron pair donor.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251-259. The Hammett constant values are generally negative for electron donating groups ($\sigma[P]=-0.66$ for $NH_2$) and positive for electron withdrawing groups ($\sigma[P]=0.78$ for a nitro group), $\sigma [P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "charge-diffuse anion" as used herein is a non-Lewis acid containing polyatomic anion having a van der Waals volume exceeding 100 Å$^3$. Charge-diffuse anions include, for example, boron tetrafluoride, boron tetraphenyl, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide or bis(p-toluenesulfonyl)amide.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "bicyclo-ring" as used herein refers to a bridged ring system such as a quinuclidine (shown below).

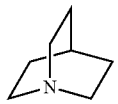

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho (o-), meta (m-) and para (p-) are art-recognized and apply to 1,2-, 1,3- and 1,4-disubstituted benzenes, respectively. For example, the names 1,2-dimethylbenzene, ortho-dimethylbenzene and o-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams, such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, fluoroalkyl (such as trifluromethyl), cyano, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, fluoroalkyl (such as trifluromethyl), cyano, or the like.

The term "carbocycle" is art recognized and includes an aromatic or non-aromatic ring in which each atom of the ring is carbon. The flowing art-recognized terms have the following meanings: "nitro" means —$NO_2$; the term "halogen" designates —F, —Cl, —Br or —I; the term "sulfhydryl" means —SH; the term "hydroxyl" means —OH; and the term "sulfonyl" means —$SO_2^-$.

The terms "amine" and "amino" are art-recognized and include both unsubstituted and substituted amines, e.g., a moiety that may be represented by the general formulas:

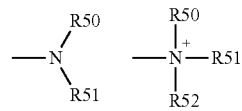

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

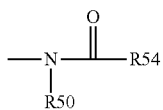

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

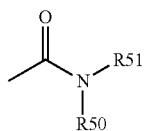

wherein R50 and R51 are as defined above. Certain embodiments of the amide in the present invention will not include amides which may be unstable.

The term "alkylthio" is art recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethylthio, and the like.

The term "carbonyl" is art recognized and includes such moieties as may be represented by the general formulas:

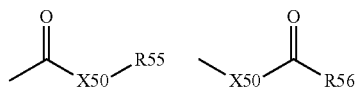

wherein X50 is a bond or represents an oxygen or a sulfur, and R55 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 is not hydrogen, the formula represents an "ester". Where X50 is an oxygen, and R55 is as first defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "oxime" and "oxime ether" are art-recognized and refer to moieties that may be represented by the general formula:

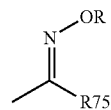

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and includes a moiety that may be represented by the general formula:

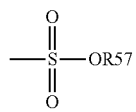

in which R57 is an electron pair, hydrogen, alkyl, cycloalkyl, or aryl.

The term "sulfate" is art recognized and includes a moiety that may be represented by the general formula:

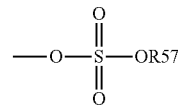

in which R57 is as defined above.

The term "sulfonamido" is art recognized and includes a moiety that may be represented by the general formula:

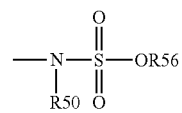

in which R50 and R56 are as defined above.

The term "sulfamoyl" is art-recognized and includes a moiety that may be represented by the general formula:

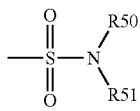

in which R50 and R51 are as defined above.

The term "sulfonyl" is art recognized and includes a moiety that may be represented by the general formula:

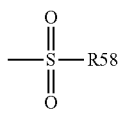

in which R58 is one of the following: hydrogen, alkyl, alkenyl, alkynyl, cycloalkyl, heterocyclyl, aryl or heteroaryl.

The term "sulfoxido" is art recognized and includes a moiety that may be represented by the general formula:

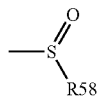

in which R58 is defined above.

The term "phosphoryl" is art-recognized and may in general be represented by the formula:

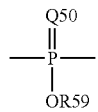

wherein Q50 represents S or O, and R59 represents hydrogen, a lower alkyl or an aryl. When used to substitute, e.g., an alkyl, the phosphoryl group of the phosphorylalkyl may be represented by the general formulas:

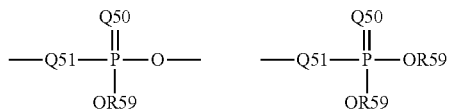

wherein Q50 and R59, each independently, are defined above, and Q51 represents O, S or N. When Q50 is S, the phosphoryl moiety is a "phosphorothioate".

The term "phosphoramidite" is art recognized and includes moieties represented by the general formulas:

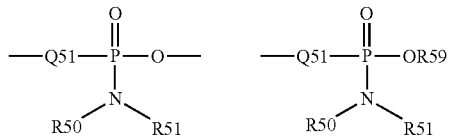

wherein Q51, R50, R51 and R59 are as defined above.

The term "phosphonamidite" is art recognized and includes moieties represented by the general formulas:

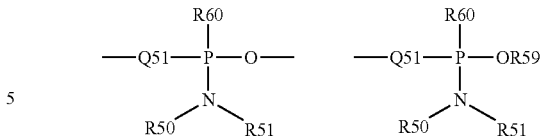

wherein Q51, R50, R51 and R59 are as defined above, and R60 represents a lower alkyl or an aryl.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms, such as nitrogen may have hydrogen substituents and/or any permissible substituents of organic compounds described herein which satisfy the valences of the heteroatoms. This invention is not intended to be limited in any manner by the permissible substituents of organic compounds.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, etc., when it occurs more than once in any structure, is intended to be independent of its definition elsewhere in the same structure unless otherwise indicated expressly or by the context.

For purposes of the invention, the chemical elements are identified in accordance with the Periodic Table of the Elements, CAS version, Handbook of Chemistry and Physics, 67th Ed., 1986-87, inside cover.

Sulfonate Anion-Containing Salts. One aspect of the invention relates to a salt represented by

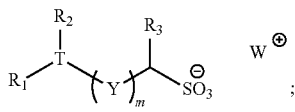

wherein, independently for each occurrence,

W represents an ammonium cation, a phosphonium cation, a heterocyclic cation, an alkali metal cation or an alkaline earth metal cation;

T represents N or P;

Y represents $CH_2$, CHF, $CF_2$ or Z—O—Z;

Z represents $CH_2$, CHF or $CF_2$;

$R_1$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_2$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, bicyclic ring, tricyclic ring, bicyclic or tricyclic fused ring, —$(CH_2)_n$—$R_8$, —C(=O)$OR_8$, —C(=O)N$(R_8)_2$, —C(=O)$SR_8$, —C(=O)$R_8$, —C(=$NR_8$)$R_8$, —C(=S)$R_8$, —C($R_8$)=C$(R_8)_2$, —C≡$CR_8$, —CH$(R_8)_2$, —C$(R_8)_3$, or —$(CH_2)_n$—$NH_2$;

$R_8$ represents independently for each occurrence —$(CH_2)_n$—$CH_3$, cycloalkyl, aryl, or heteroaryl;

m represents independently for each occurrence an integer in the range 1-10 inclusive; and n represents independently for each occurrence an integer in the range 1-10 inclusive.

In certain embodiments, the invention relates to any of the aforementioned salts, wherein the salt is represented by

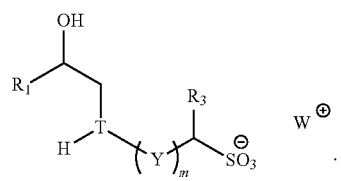

In certain embodiments, the invention relates to any of the aforementioned salts, wherein the salt is represented by

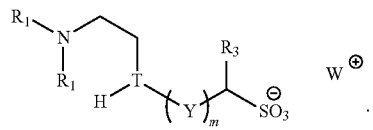

In certain embodiments, the invention relates to any of the aforementioned salts, wherein W is an ammonium, pyridinium, imidazolium, benzimidazolium, pyrazolium, benzpyrazolium, indazolium, thiazolium, benzothiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium.

In certain embodiments, the invention relates to any of the aforementioned salts, wherein W is

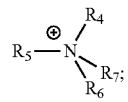

$R_4$ and $R_5$ represent independently for each occurrence alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —$(CH_2)_n$—$R_8$, —C$(R_8)$=C$(R_8)_2$, —C≡$CR_8$, —CH$(R_8)_2$, or —C$(R_8)_3$; or $R_4$ and $R_5$ taken together with the nitrogen to which they are attached form a five-, six-, or seven-membered heterocyclic ring; $R_6$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —$(CH_2)_n$—$R_8$, —C$(R_8)$=C$(R_8)_2$, —C≡$CR_8$, —CH$(R_8)_2$, or —C$(R_8)_3$; and $R_7$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —$(CH_2)_n$—$R_8$, —C$(R_8)$=C$(R_8)_2$, —C≡$CR_8$, —CH$(R_8)_2$, or —C$(R_8)_3$.

In certain embodiments, the invention relates to any of the aforementioned salts, wherein T represents N.

In certain embodiments, the invention relates to any of the aforementioned salts, wherein Y represents $CH_2$, CHF or $CF_2$. In certain embodiments, the invention relates to any of the aforementioned salts, wherein Y represents $CH_2$. In certain embodiments, the invention relates to any of the aforementioned salts, wherein Y represents $CF_2$. In certain embodiments, the invention relates to any of the aforementioned salts, wherein only one Y represents Z—O—Z. In certain embodiments, the invention relates to any of the aforementioned salts, wherein only one Y represents Z—O—Z; and Z is $CH_2$. In certain embodiments, the invention relates to any of the aforementioned salts, wherein only one Y represents Z—O—Z; and Z is $CF_2$.

In certain embodiments, the invention relates to any of the aforementioned salts, wherein $R_1$ is hydrogen. In certain embodiments, the invention relates to any of the aforementioned salts, wherein $R_1$ is not hydrogen. In certain embodiments, the invention relates to any of the aforementioned salts, wherein $R_1$ represents alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl. In certain embodiments, the invention relates to any of the aforementioned salts, wherein $R_1$ is alkyl, aryl or aralkyl. In certain embodiments, the invention relates to any of the aforementioned salts, wherein $R_1$ is alkyl. In certain embodiments, the invention relates to any of the aforementioned salts, wherein $R_1$ represents ethyl, n-hexyl, 1,5-dimethylhexyl, 2-ethylhexyl, 2-heptyl, isopropyl, isobutyl, or 2-hydroxyethyl.

In certain embodiments, the invention relates to any of the aforementioned salts, wherein $R_2$ is alkyl, aryl or aralkyl. In certain embodiments, the invention relates to any of the aforementioned salts, wherein $R_2$ is alkyl.

In certain embodiments, the invention relates to any of the aforementioned salts, wherein $R_3$ is hydrogen or alkyl.

In certain embodiments, the invention relates to any of the aforementioned salts, wherein $R_4$, $R_5$, $R_6$, and $R_7$ represent alkyl.

In certain embodiments, the invention relates to any of the aforementioned salts, wherein m is 2 or 3.

In certain embodiments, the invention relates to any of the aforementioned salts, wherein the salt is represented by

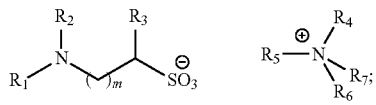

$R_1$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl; $R_2$ represents alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl; $R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)$=$C(R_8)_2$, —C≡$CR_8$, —$CH(R_8)_2$, or —$C(R_8)_3$; $R_4$, $R_5$, $R_6$, and $R_7$ represent independently for each occurrence methyl, ethyl, or n-butyl; and $R_8$ represents independently for each occurrence —$(CH_2)_n$—$CH_3$, cycloalkyl, aryl, or heteroaryl.

In certain embodiments, the invention relates to any of the aforementioned salts, wherein the salt is represented by

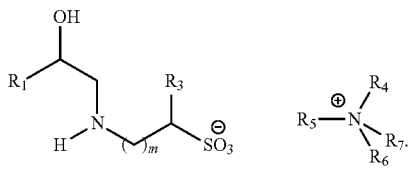

In certain embodiments, the invention relates to any of the aforementioned salts, wherein the salt is represented by

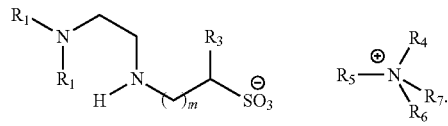

In certain embodiments, the invention relates to any of the aforementioned salts, wherein $R_1$ represents ethyl, n-hexyl, 1,5-dimethylhexyl, 2-ethylhexyl, 2-heptyl, isopropyl, isobutyl, or 2-hydroxyethyl; and $R_3$ represents H or methyl.

In certain embodiments, the invention relates to any of the aforementioned salts, wherein $R_1$ represents ethyl, n-hexyl, 1,5-dimethylhexyl, 2-ethylhexyl, 2-heptyl, isopropyl, isobutyl, or 2-hydroxyethyl; $R_3$ represents H or methyl; and $R_4$, $R_5$, $R_6$, and $R_7$ represent independently for each occurrence methyl, ethyl, or n-butyl.

In certain embodiments, the invention relates to any of the aforementioned salts, wherein $R_1$ represents ethyl, n-hexyl, 1,5-dimethylhexyl, 2-ethylhexyl, 2-heptyl, isopropyl, isobutyl, or 2-hydroxyethyl; $R_3$ represents H or methyl; $R_4$, $R_5$, $R_6$, and $R_7$ represent independently for each occurrence methyl, ethyl, or n-butyl; and m is 2 or 3.

In certain embodiments, the invention relates to any of the aforementioned salts, wherein $R_1$ represents alkyl, aryl or aralkyl; and $R_3$ represents H or methyl.

In certain embodiments, the invention relates to any of the aforementioned salts, wherein $R_1$ represents alkyl, aryl or aralkyl; $R_3$ represents H or methyl; and $R_4$, $R_5$, $R_6$, and $R_7$ represent independently for each occurrence methyl, ethyl, or n-butyl.

In certain embodiments, the invention relates to any of the aforementioned salts, wherein $R_1$ represents alkyl, aryl or aralkyl; $R_3$ represents H or methyl; $R_4$, $R_5$, $R_6$, and $R_7$ represent independently for each occurrence methyl, ethyl, or n-butyl; and m is 2 or 3.

Another aspect of the invention relates to the salts formed when the salts described above are used to sequester a gas (as described below). In addition, the invention also encompasses the resulting salts formed when the gas-containing salts are heated (as described below).

Sulfonic Acid-Containing Salts. One aspect of the invention relates to a salt represented by

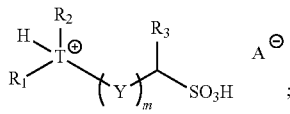

wherein, independently for each occurrence,

A represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)-(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, tris(perfluoroalkyl)trifluorophosphate anion, or an anionic site of a cation-exchange resin;

T represents N or P;

Y represents $CH_2$, CHF, $CF_2$ or Z—O—Z;

Z represents $CH_2$, CHF or $CF_2$;

$R_1$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_2$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, bicyclic ring, tricyclic ring, bicyclic or tricyclic fused ring, —$(CH_2)_n$—$R_8$, —C(=O)$OR_8$, —C(=O)N$(R_8)_2$, —C(=O)$SR_8$, —C(=O)$R_8$, —C(=N$R_8$)$R_8$, —C(=S)$R_8$, —C$(R_8)$=C$(R_8)_2$, —C≡C$R_8$, —CH$(R_8)_2$, —C$(R_8)_3$, —$(CH_2)_n$—$NH_2$;

$R_8$ represents independently for each occurrence —$(CH_2)_n$—$CH_3$, cycloalkyl, aryl, or heteroaryl;

m represents independently for each occurrence an integer in the range 1-10 inclusive; and n represents independently for each occurrence an integer in the range 1-10 inclusive.

In certain embodiments, the invention relates to any of the aforementioned salts, wherein the salt is represented by

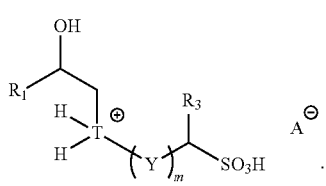

In certain embodiments, the invention relates to any of the aforementioned salts, wherein the salt is represented by

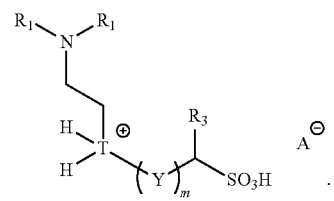

In certain embodiments, the invention relates to any of the aforementioned salts, wherein A represents $I^{-1}$, $Br^{-1}$, $Cl^{-1}$, $HSO_4^{-1}$, $CH_3SO_3^{-1}$, $NO_3^{-1}$, $ClO_3^{-1}$, $FSO_3^{-1}$, $CF_3SO_3^{-1}$, $(CF_3SO_2)_2N^{-1}$, tris(perfluoroalkyl)-trifluorophosphate (FAP) anions, or a tetrafluoroethylene-perfluoro-3,6-dioxa-4-methyl-7-octenesulfonic acid copolymer (Nafion).

In certain embodiments, the invention relates to any of the aforementioned salts, wherein T represents N.

In certain embodiments, the invention relates to any of the aforementioned salts, wherein Y represents $CH_2$, CHF or $CF_2$. In certain embodiments, the invention relates to any of the aforementioned salts, wherein Y represents $CH_2$. In certain embodiments, the invention relates to any of the aforementioned salts, wherein Y represents $CF_2$. In certain embodiments, the invention relates to any of the aforementioned salts, wherein only one Y represents Z—O—Z. In certain embodiments, the invention relates to any of the aforementioned salts, wherein only one Y represents Z—O—Z; and Z is $CH_2$. In certain embodiments, the invention relates to any of the aforementioned salts, wherein only one Y represents Z—O—Z; and Z is $CF_2$.

In certain embodiments, the invention relates to any of the aforementioned salts, wherein $R_1$ is hydrogen. In certain embodiments, the invention relates to any of the aforementioned salts, wherein $R^1$ is not hydrogen. In certain embodiments, the invention relates to any of the aforementioned salts, wherein $R_1$ is alkyl, aryl or aralkyl. In certain embodiments, the invention relates to any of the aforementioned salts, wherein $R_1$ is alkyl.

In certain embodiments, the invention relates to any of the aforementioned salts, wherein $R_2$ is alkyl, aryl or aralkyl. In certain embodiments, the invention relates to any of the aforementioned salts, wherein $R_2$ is alkyl.

In certain embodiments, the invention relates to any of the aforementioned salts, wherein $R_3$ is hydrogen or alkyl.

In certain embodiments, the invention relates to any of the aforementioned salts, wherein m is 2 or 3.

In certain embodiments, the invention relates to any of the aforementioned salts, wherein $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —C$(R_8)$=C$(R_8)_2$, —C≡C$R_8$—CH$(R_8)_2$, or —C$(R_8)_3$; and $R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —C$(R_8)$=C$(R_8)_2$, —C≡C$R_8$—CH$(R_8)_2$, or —C$(R_8)_3$.

In certain embodiments, the invention relates to any of the aforementioned salts, wherein T represents N; $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —C$(R_8)$=C$(R_8)_2$, —C≡C$R_8$, —CH$(R_8)_2$, or —C$(R_8)_3$; and $R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —C$(R_8)$=C≡C$R_8$, —CH$(R_8)_2$, or —C$(R_8)_3$.

In certain embodiments, the invention relates to any of the aforementioned salts, wherein the salt is represented by

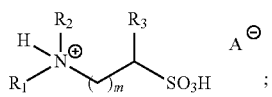

A represents $I^{-1}$, $Br^{-1}$, $Cl^{-1}$, $HSO_4^{-1}$, $CH_3SO_3^{-1}$, $NO_3^{-1}$, $ClO_3^{-1}$, $FSO_3^{-1}$, $CF_3SO_3^{-1}$, $(CF_3SO_2)_2N^{-1}$, tris(perfluoroalkyl)-trifluorophosphate (FAP) anions, or a tetrafluoroethylene-perfluoro-3,6-dioxa-4-methyl-7-octenesulfonic acid copolymer (Naftion); $R_1$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl; $R_2$ represents alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl; $R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$; and $R_8$ represents independently for each occurrence $-(CH_2)_n-CH_3$, cycloalkyl, aryl, or heteroaryl.

In certain embodiments, the invention relates to any of the aforementioned salts, wherein the salt is represented by

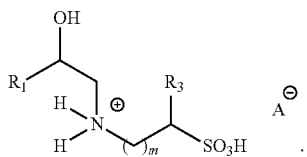

In certain embodiments, the invention relates to any of the aforementioned salts, wherein the salt is represented by

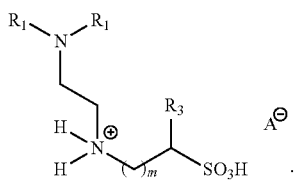

In certain embodiments, the invention relates to any of the aforementioned salts, wherein $R_1$ represents n-hexyl, 1,5-dimethylhexyl, 2-ethylhexyl, 2-heptyl, isopropyl, isobutyl, or 2-hydroxyethyl; and $R_3$ represents H or methyl.

In certain embodiments, the invention relates to any of the aforementioned salts, wherein $R_1$ represents n-hexyl, 1,5-dimethylhexyl, 2-ethylhexyl, 2-heptyl, isopropyl, isobutyl, or 2-hydroxyethyl; $R_3$ represents H or methyl; and $R_4$, $R_5$, $R_6$, and $R_7$ represent independently for each occurrence methyl, ethyl, or n-butyl.

In certain embodiments, the invention relates to any of the aforementioned salts, wherein $R_1$ represents n-hexyl, 1,5-dimethylhexyl, 2-ethylhexyl, 2-heptyl, isopropyl, isobutyl, or 2-hydroxyethyl; $R_3$ represents H or methyl; $R_4$, $R_5$, $R_6$, and $R_7$ represent independently for each occurrence methyl, ethyl, or n-butyl; and m is 2 or 3.

In certain embodiments, the invention relates to any of the aforementioned salts, wherein $R_1$ represents alkyl, aryl or aralkyl; and $R_3$ represents H or methyl.

In certain embodiments, the invention relates to any of the aforementioned salts, wherein $R_1$ represents alkyl, aryl or aralkyl; $R_3$ represents H or methyl; and m is 2 or 3.

Another aspect of the invention relates to the salts formed when the salts described above are used to sequester a gas (as described below). In addition, the invention also encompasses the resulting salts formed when the gas-containing salts are heated (as described below).

Aryl- and Heteroaryl-Containing Salts. One aspect of the invention relates to a salt represented by

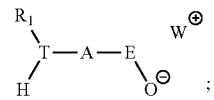

wherein, independently for each occurrence,

W represents an ammonium cation, a phosponium cation, a heterocyclic cation, an alkali metal cation or an alkaline earth metal cation;

T represents N or P;

E represents $-C(=O)-$ or $-S(=O)_2-$;

A represents an aryl or heteroaryl diradical;

$R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_4$ and $R_5$ represent independently for each occurrence alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, $-(CH_2)_n-R_8$, $-C(R_8)=C(R_8)_2$, $-C\equiv CR_8$, $-CH(R_8)_2$, or $-C(R_8)_3$; or $R_4$ and $R_5$ taken together with the nitrogen to which they are attached form a five-, six-, or seven-membered heterocyclic ring;

$R_6$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, $-(CH_2)_n-R8$, $-C(R_8)=C(R_8)_2$, $-C\equiv CR_8$, $-CH(R_8)_2$, or $-C(R_8)_3$;

$R_7$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, $-(CH_2)_n-R_8$, $-C(R_8)=C(R_8)_2$, $-C\equiv CR_8$, $-CH(R_8)_2$, or $-C(R_8)_3$;

$R_8$ represents independently for each occurrence $-(CH_2)_n-CH_3$, cycloalkyl, aryl, or heteroaryl;

m represents independently for each occurrence an integer in the range 1-10 inclusive; and n represents independently for each occurrence an integer in the range 1-10 inclusive.

In certain embodiments, the invention relates to any of the aforementioned salts, wherein W is an ammonium, pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium.

In certain embodiments, the invention relates to any of the aforementioned salts, wherein W is

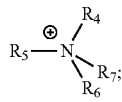

$R_4$ and $R_5$ represent independently for each occurrence alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —$(CH_2)_n$—$R_8$, —$C(R_8)$=C$(R_8)_2$, —C≡$CR_8$—$CH(R_8)_2$, or —$C(R_8)_3$; or $R_4$ and $R_5$ taken together with the nitrogen to which they are attached form a five-, six-, or seven-membered heterocyclic ring; $R_6$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —$(CH_2)_n$—$R_8$, —$C(R_8)$=$C(R_8)_2$, —C≡$CR_8$, —$CH(R_8)_2$, or —$C(R_8)_3$; and $R_7$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —$(CH_2)_n$—$R_8$, —$C(R_8)$=$C(R_8)_2$, —≡$CR_8$, —$CH(R_8)_2$, or —$C(R_8)_3$.

In certain embodiments, the invention relates to any of the aforementioned salts, wherein T represents N.

In certain embodiments, the invention relates to any of the aforementioned salts, wherein E represents —C(=O)—. In certain embodiments, the invention relates to any of the aforementioned salts, wherein E represents —S(=O)$_2$—.

In certain embodiments, the invention relates to any of the aforementioned salts, wherein $R_1$ is alkyl, aryl or aralkyl. In certain embodiments, the invention relates to any of the aforementioned salts, wherein $R_1$ is alkyl.

In certain embodiments, the invention relates to any of the aforementioned salts, wherein $R_3$ is hydrogen or alkyl.

In certain embodiments, the invention relates to any of the aforementioned salts, wherein $R_4$, $R_5$, $R_6$, and $R_7$ is alkyl.

In certain embodiments, the invention relates to any of the aforementioned salts, wherein A is an aryl diradical. In certain embodiments, the invention relates to any of the aforementioned salts, wherein A is an benzene diradical.

In certain embodiments, the invention relates to any of the aforementioned salts, wherein T represents N; $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)$=$C(R_8)_2$, —C≡$CR_8$, —$CH(R_8)_2$, or —$C(R_8)_3$; and A is an aryl diradical.

In certain embodiments, the invention relates to any of the aforementioned salts, wherein T represents N; $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)$=$C(R_8)_2$, —C≡$CR_8$, —$CH(R_8)_2$, or —$C(R_8)_3$; and A is an aryl diradical; and $R_4$, $R_5$, $R_6$, and $R_7$ represent independently for each occurrence methyl, ethyl, or n-butyl.

In certain embodiments, the invention relates to any of the aforementioned salts, wherein $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)$=$C(R_8)_2$, —C≡$CR_8$, —$CH(R_8)_2$, or —$C(R_8)_3$; and A is an aryl diradical.

In certain embodiments, the invention relates to any of the aforementioned salts, wherein $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)$=$C(R_8)_2$, —C≡$CR_8$, —$CH(R_8)_2$, or —$C(R_8)_3$; and A is an aryl diradical; and $R_4$, $R_5$, $R_6$, and $R_7$ represent independently for each occurrence methyl, ethyl, or n-butyl.

In certain embodiments, the invention relates to any of the aforementioned salts, wherein $R_4$, $R_5$, $R_6$, and $R_7$ represent independently for each occurrence methyl, ethyl, or n-butyl.

In certain embodiments, the invention relates to any of the aforementioned salts, wherein the salt is represented by

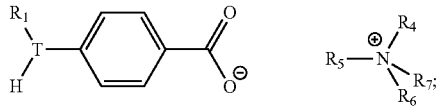

$R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl or —$CH_2CH(OH)$—$R_8$ or —$CH_2CHN(R_8)_2$; $R_4$, $R_5$, $R_6$, and $R_7$ represent independently for each occurrence methyl, ethyl, or n-butyl; and $R_8$ represents alkyl, aryl or aralkyl.

In certain embodiments, the invention relates to any of the aforementioned salts, wherein $R_1$ represents alkyl, aryl or aralkyl. In certain embodiments, the invention relates to any of the aforementioned salts, wherein $R_1$ represents —$CH_2CH(OH)$—$R_8$ or —$CH_2CHN(R_8)_2$. In certain embodiments, the invention relates to any of the aforementioned salts, wherein $R_1$ represents alkyl, aryl or aralkyl; and $R_4$, $R_5$, $R_6$, and $R_7$ represent independently for each occurrence methyl, ethyl, or n-butyl.

Another aspect of the invention relates to a salt represented by

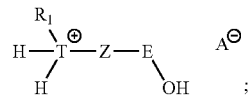

wherein, independently for each occurrence,

A represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)-(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, tris(perfluoroalkyl)trifluorophosphate anion, or an anionic site of a cation-exchange resin;

T represents N or P;

E represents —C(=O)— or —S(=O)$_2$—;

Z represents an aryl or heteroaryl diradical;

$R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_8$ represents independently for each occurrence —$(CH_2)_n$—$CH_3$, cycloalkyl, aryl, or heteroaryl;

m represents independently for each occurrence an integer in the range 1-10 inclusive; and n represents independently for each occurrence an integer in the range 1-10 inclusive.

In certain embodiments, the invention relates to any of the aforementioned salts, wherein A represents $I^{-1}$, $Br^{-1}$, $Cl^{-1}$, $HSO_4^{-1}$, $CH_3SO_3^{-1}$, $NO_3^{-1}$, $ClO_3^{-1}$, $FSO_3^{-1}$, $CF_3SO_3^{-1}$, $(CF_3SO_2)_2N^{-1}$, tris(perfluoroalkyl)-trifluorophosphate (FAP) anions, or a tetrafluoroethylene-perfluoro-3,6-dioxa-4-methyl-7-octenesulfonic acid copolymer (Naftion).

In certain embodiments, the invention relates to any of the aforementioned salts, wherein T represents N.

In certain embodiments, the invention relates to any of the aforementioned salts, wherein E represents —C(=O)—. In certain embodiments, the invention relates to any of the aforementioned salts, wherein E represents —S(=O)$_2$—.

In certain embodiments, the invention relates to any of the aforementioned salts, wherein $R_1$ is alkyl, aryl or aralkyl. In certain embodiments, the invention relates to any of the aforementioned salts, wherein $R_1$ is alkyl.

In certain embodiments, the invention relates to any of the aforementioned salts, wherein $R_3$ is hydrogen or alkyl.

In certain embodiments, the invention relates to any of the aforementioned salts, wherein Z is an aryl diradical. In certain embodiments, the invention relates to any of the aforementioned salts, wherein Z is an benzene diradical.

In certain embodiments, the invention relates to any of the aforementioned salts, wherein $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)=C(R_8)_2$, —$C\equiv CR_8$, —$CH(R_8)_2$, or —$C(R_8)_3$; and Z is an aryl diradical.

In certain embodiments, the invention relates to any of the aforementioned salts, wherein T represents N; $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)=C(R_8)_2$, —$C\equiv CR_8$, —$CH(R_8)_2$, or —$C(R_8)_3$; and Z is an aryl diradical.

In certain embodiments, the invention relates to any of the aforementioned salts, wherein the salt is represented by

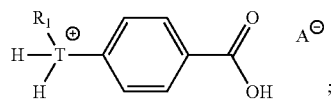

$R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl —$CH_2CH(OH)$—$R_8$ or —$CH_2CHN(R_8)_2$; and $R_8$ represents alkyl, aryl or aralkyl.

In certain embodiments, the invention relates to any of the aforementioned salts, wherein $R_1$ represents alkyl, aryl or aralkyl. In certain embodiments, the invention relates to any of the aforementioned salts, wherein $R_1$ represents —$CH_2CH$(OH)—$R_8$ or —$CH_2CHN(R_8)_2$. In certain embodiments, the invention relates to any of the aforementioned salts, wherein $R_1$ represents alkyl, aryl or aralkyl.

Another aspect of the invention relates to the salts formed when the salts described above are used to sequester a gas (as described below). In addition, the invention also encompasses the resulting salts formed when the gas-containing salts are heated (as described below).

Methods of Sequestering a Gas. One aspect of the invention relates to sequestering a gas by contacting the gas with an ionic liquid. In certain embodiments, one of the components in the ionic liquid comprises a nucleophic moiety which can react with the gas to covalently bind the gas to one of the components of the ionic liquid, thereby sequestering it.

In certain embodiments, the invention relates to a method of sequestering a gas, comprising contacting the gas with a salt represented by any of the aforementioned salts.

In certain embodiments, the invention relates to the aforementioned method, wherein the salt is sulfonate anion-containing salt (as described above).

In certain embodiments, the invention relates to the aforementioned method, wherein the salt is sulfonic acid-containing salt (as described above).

In certain embodiments, the invention relates to the aforementioned method, wherein the salt is aryl- or heteroaryl-containing salt (as described above).

In certain embodiments, the invention relates to the aforementioned method, wherein the gas is $CO_2$, $CS_2$, $SO_2$ or $NO_2$.

In certain embodiments, the invention relates to the aforementioned method, wherein the gas is $CO_2$.

Method of Releasing a Gas. One aspect of the invention relates to releasing a gas by heating a salt which had previously been used to sequested a gas (see above). In certain embodiments, a covalent bond links the gas to the salt. In other embodiments, a noncovalent association links the gas to the salt. By heating a composition comprising a salt to which a gas is bound covalently or associated noncovalently, the gas can be released.

In certain embodiments, the invention relates to a method of releasing a gas, comprising the step of heating a composition comprising a gas dissolved in a salt; wherein the salt is represented by any of the aforementioned salts.

In certain embodiments, the invention relates to the aforementioned method, wherein the salt is sulfonate anion-containing salt (as described above).

In certain embodiments, the invention relates to the aforementioned method, wherein the salt is sulfonic acid-containing salt (as described above).

In certain embodiments, the invention relates to the aforementioned method, wherein the salt is aryl- or heteroaryl-containing salt (as described above).

In certain embodiments, the invention relates to the aforementioned method, wherein the gas is $CO_2$, $CS_2$, $SO_2$ or $NO_2$.

In certain embodiments, the invention relates to the aforementioned method, wherein the gas is $CO_2$.

In certain embodiments, the invention relates to a method of releasing a gas, comprising the step of heating a salt; wherein the salt is represented by

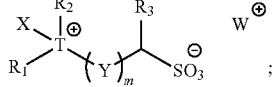

wherein, independently for each occurrence,

X represents —$CO_2^{-1}$, —$CS_2^{-1}$, —$SO^{-1}$ or —$NO_2^{-1}$;

W represents an ammonium cation, a phosponium cation, a heterocyclic cation, an alkali metal cation or an alkaline earth metal cation;

T represents N or P;

Y represents CH$_2$, CHF, CF$_2$ or Z—O—Z;

Z represents CH$_2$, CHF or CF$_2$;

R$_1$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

R$_2$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

R$_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, bicyclic ring, tricyclic ring, bicyclic or tricyclic fused ring, —(CH$_2$)$_n$—R$_8$, —C(=O)OR$_8$, —C(=O)N(R$_8$)$_2$, —C(=O)SR$_8$, —C(=O)R$_8$, —C(=NR$_8$)R$_8$, —C(=S)R$_8$, —C(R$_8$)=C(R$_8$)$_2$, —C≡CR$_8$, —CH(R$_8$)$_2$, —C(R$_8$)$_3$, or —(CH$_2$)$_n$—NH$_2$;

R$_8$ represents independently for each occurrence —(CH$_2$)$_n$—CH$_3$, cycloalkyl, aryl, or heteroaryl;

m represents independently for each occurrence an integer in the range 1-10 inclusive; and n represents independently for each occurrence an integer in the range 1-10 inclusive.

In certain embodiments, the invention relates to any of the aforementioned methods, wherein the salt is represented by

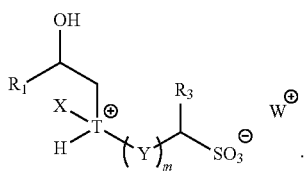

In certain embodiments, the invention relates to any of the aforementioned methods, wherein the salt is represented by

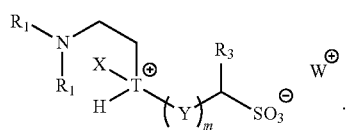

In certain embodiments, the invention relates to any of the aforementioned methods, wherein X is —CO$_2$$^{-1}$.

In certain embodiments, the invention relates to any of the aforementioned methods, wherein W is an ammonium, pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium.

In certain embodiments, the invention relates to any of the aforementioned methods, wherein W is

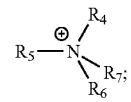

R$_4$ and R$_5$ represent independently for each occurrence alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —(CH$_2$)$_n$—R$_8$, —C(R$_8$)=C(R$_8$)$_2$, —C≡CR$_8$, —CH(R$_8$)$_2$, or —C(R$_8$)$_3$; or R$_4$ and R$_5$ taken together with the nitrogen to which they are attached form a five-, six-, or seven-membered heterocyclic ring; R$_6$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —(CH$_2$)$_n$—R$_8$, —C(R$_8$)=C(R$_8$)$_2$, —C≡CR$_8$, —CH(R$_8$)$_2$, or —C(R$_8$)$_3$; and R$_7$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —(CH$_2$)$_n$—R$_8$, —C(R$_8$)=C(R$_8$)$_2$, —C≡CR$_8$, —CH(R$_8$)$_2$, or —C(R$_8$)$_3$.

In certain embodiments, the invention relates to any of the aforementioned methods, wherein T represents N.

In certain embodiments, the invention relates to any of the aforementioned methods, wherein Y represents CH$_2$, CHF or CF$_2$. In certain embodiments, the invention relates to any of the aforementioned methods, wherein Y represents CH$_2$. In certain embodiments, the invention relates to any of the aforementioned methods, wherein Y represents CF$_2$. In certain embodiments, the invention relates to any of the aforementioned methods, wherein only one Y represents Z—O—Z. In certain embodiments, the invention relates to any of the aforementioned methods, wherein only one Y represents Z—O—Z; and Z is CH$_2$. In certain embodiments, the invention relates to any of the aforementioned methods, wherein only one Y represents Z—O—Z; and Z is CF$_2$.

In certain embodiments, the invention relates to any of the aforementioned methods, wherein R$_1$ is hydrogen. In certain embodiments, the invention relates to any of the aforementioned methods, wherein R$_1$ is not hydrogen. In certain embodiments, the invention relates to any of the aforementioned methods, wherein R$_1$ represents alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl. In certain embodiments, the invention relates to any of the aforementioned methods, wherein R$_1$ is alkyl, aryl or aralkyl. In certain embodiments, the invention relates to any of the aforementioned methods, wherein R$_1$ is alkyl. In certain embodiments, the invention relates to any of the aforementioned methods, wherein R$_1$ represents ethyl, n-hexyl, 1,5-dimethylhexyl, 2-ethylhexyl, 2-heptyl, isopropyl, isobutyl, or 2-hydroxyethyl.

In certain embodiments, the invention relates to any of the aforementioned methods, wherein $R_2$ is alkyl, aryl or aralkyl. In certain embodiments, the invention relates to any of the aforementioned methods, wherein $R_2$ is alkyl.

In certain embodiments, the invention relates to any of the aforementioned methods, wherein $R_3$ is hydrogen or alkyl.

In certain embodiments, the invention relates to any of the aforementioned methods, wherein $R_4$, $R_5$, $R_6$, and $R_7$ represent alkyl.

In certain embodiments, the invention relates to any of the aforementioned methods, wherein m is 2 or 3.

In certain embodiments, the invention relates to any of the aforementioned methods, wherein the salt is represented by

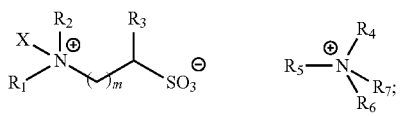

$R_1$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl; $R_2$ represents alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl; $R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8-CH(R_8)_2$, or $-C(R_8)_3$; $R_4$, $R_5$, $R_6$, and $R_7$ represent independently for each occurrence methyl, ethyl, or n-butyl; and $R_8$ represents independently for each occurrence $-(CH_2)_n-CH_3$, cycloalkyl, aryl, or heteroaryl.

In certain embodiments, the invention relates to any of the aforementioned methods, wherein the salt is represented by

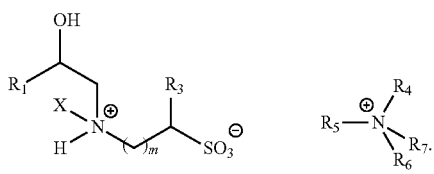

In certain embodiments, the invention relates to any of the aforementioned methods, wherein the salt is represented by

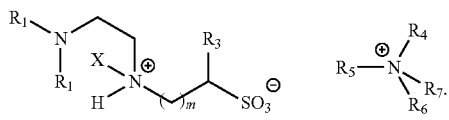

In certain embodiments, the invention relates to any of the aforementioned methods, wherein $R_1$ represents ethyl, n-hexyl, 1,5-dimethylhexyl, 2-ethylhexyl, 2-heptyl, isopropyl, isobutyl, or 2-hydroxyethyl; and $R_3$ represents H or methyl.

In certain embodiments, the invention relates to any of the aforementioned methods, wherein $R_1$ represents ethyl, n-hexyl, 1,5-dimethylhexyl, 2-ethylhexyl, 2-heptyl, isopropyl, isobutyl, or 2-hydroxyethyl; $R_3$ represents H or methyl; and $R_4$, $R_5$, $R_6$, and $R_7$ represent independently for each occurrence methyl, ethyl, or n-butyl.

In certain embodiments, the invention relates to any of the aforementioned methods, wherein $R_1$ represents ethyl, n-hexyl, 1,5-dimethylhexyl, 2-ethylhexyl, 2-heptyl, isopropyl, isobutyl, or 2-hydroxyethyl; $R_3$ represents H or methyl; $R_4$, $R_5$, $R_6$, and $R_7$ represent independently for each occurrence methyl, ethyl, or n-butyl; and m is 2 or 3.

In certain embodiments, the invention relates to any of the aforementioned methods, wherein $R_1$ represents alkyl, aryl or aralkyl; and $R_3$ represents H or methyl.

In certain embodiments, the invention relates to any of the aforementioned methods, wherein $R_1$ represents alkyl, aryl or aralkyl; $R_3$ represents H or methyl; and $R_4$, $R_5$, $R_6$, and $R_7$ represent independently for each occurrence methyl, ethyl, or n-butyl.

In certain embodiments, the invention relates to any of the aforementioned methods, wherein $R_1$ represents alkyl, aryl or aralkyl; $R_3$ represents H or methyl; $R_4$, $R_5$, $R_6$, and $R_7$ represent independently for each occurrence methyl, ethyl, or n-butyl; and m is 2 or 3.

In certain embodiments, the invention relates to a method of releasing a gas, comprising the step of heating a salt; wherein the salt is represented by

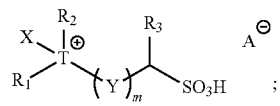

wherein, independently for each occurrence,

X represents $-CO_2^{-1}$, $-CS_2^{-1}$, $-SO_2^{-1}$ or $-NO_2^{-1}$;

A represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)-(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, tris(perfluoroalkyl)trifluorophosphate anion, or an anionic site of a cation-exchange resin;

T represents N or P;

Y represents $CH_2$, CHF, $CF_2$ or Z—O—Z;

Z represents $CH_2$, CHF or $CF_2$;

$R_1$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_2$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, bicyclic ring, tricyclic ring, bicyclic or tricyclic fused ring, —$(CH_2)_n$—$R_8$, —$C(=O)OR_8$, —$C(=O)N(R_8)_2$, —$C(=O)SR_8$, —$C(=O)R_8$, —$C(=NR_8)R_8$, —$C(=S)R_8$, —$C(R_8)=C(R_8)_2$, —$C\equiv CR_8$, —$CH(R_8)_2$, —$C(R_8)_3$, or —$(CH_2)_n$—$NH_2$;

$R_8$ represents independently for each occurrence —$(CH_2)_n$—$CH_3$, cycloalkyl, aryl, or heteroaryl;

m represents independently for each occurrence an integer in the range 1-10 inclusive; and n represents independently for each occurrence an integer in the range 1-10 inclusive.

In certain embodiments, the invention relates to any of the aforementioned methods, wherein X is —$CO_2^{-1}$.

In certain embodiments, the invention relates to any of the aforementioned methods, wherein the salt is represented by

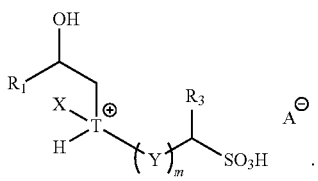

In certain embodiments, the invention relates to any of the aforementioned methods, wherein the salt is represented by

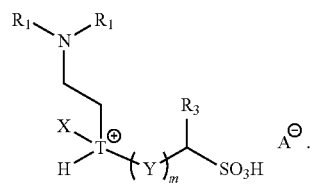

In certain embodiments, the invention relates to any of the aforementioned methods, wherein A represents $I^{-1}$, $Br^{-1}$, $Cl^{-1}$, $HSO_4^{-1}$, $CH_3SO_3^{-1}$, $NO_3^{-1}$, $ClO_3^{-1}$, $FSO_3^{-1}$, $CF_3SO_3^{-1}$, $(CF_3SO_2)_2N^{-1}$, tris(perfluoroalkyl)-trifluorophosphate (FAP) anions, or a tetrafluoroethylene-perfluoro-3,6-dioxa-4-methyl-7-octenesulfonic acid copolymer (Nafion).

In certain embodiments, the invention relates to any of the aforementioned methods, wherein T represents N.

In certain embodiments, the invention relates to any of the aforementioned methods, wherein Y represents $CH_2$, CHF or $CF_2$. In certain embodiments, the invention relates to any of the aforementioned methods, wherein Y represents $CH_2$. In certain embodiments, the invention relates to any of the aforementioned methods, wherein Y represents $CF_2$. In certain embodiments, the invention relates to any of the aforementioned methods, wherein only one Y represents Z—O—Z. In certain embodiments, the invention relates to any of the aforementioned methods, wherein only one Y represents Z—O—Z; and Z is $CH_2$. In certain embodiments, the invention relates to any of the aforementioned methods, wherein only one Y represents Z—O—Z; and Z is $CF_2$.

In certain embodiments, the invention relates to any of the aforementioned methods, wherein $R_1$ is hydrogen. In certain embodiments, the invention relates to any of the aforementioned methods, wherein $R^1$ is not hydrogen. In certain embodiments, the invention relates to any of the aforementioned methods, wherein $R_1$ is alkyl, aryl or aralkyl. In certain embodiments, the invention relates to any of the aforementioned methods, wherein $R_1$ is alkyl.

In certain embodiments, the invention relates to any of the aforementioned methods, wherein $R_2$ is alkyl, aryl or aralkyl. In certain embodiments, the invention relates to any of the aforementioned methods, wherein $R_2$ is alkyl.

In certain embodiments, the invention relates to any of the aforementioned methods, wherein $R_3$ is hydrogen or alkyl.

In certain embodiments, the invention relates to any of the aforementioned methods, wherein m is 2 or 3.

In certain embodiments, the invention relates to any of the aforementioned methods, wherein $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)=C(R_8)_2$, —$C\equiv CR_8$, —$CH(R_8)_2$, or —$C(R_8)_3$; and $R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)=C(R_8)_2$, —$C\equiv CR_8$, —$CH(R_8)_2$, or —$C(R_8)_3$.

In certain embodiments, the invention relates to any of the aforementioned methods, wherein T represents N; $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)=C(R_8)_2$, —$C\equiv CR_8$, —$CH(R_8)_2$, or —$C(R_8)_3$; and $R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)=C(R_8)_2$, —$C\equiv CR_8$, —$CH(R_8)_2$, or —$C(R_8)_3$.

In certain embodiments, the invention relates to any of the aforementioned methods, wherein the salt is represented by

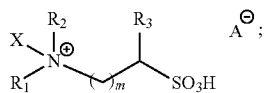

A represents $I^{-1}$, $Br^{-1}$, $Cl^{-1}$, $HSO_4^{-1}$, $CH_3SO_3^{-1}$, $NO_3^{-1}$, $ClO_3^{-1}$, $FSO_3^{-1}$, $CF_3SO_3^{-1}$, $(CF_3SO_2)_2N^{-1}$, tris(perfluoroalkyl)-trifluorophosphate (FAP) anions, or a tetrafluoroethylene-perfluoro-3,6-dioxa-4-methyl-7-octenesulfonic acid copolymer (Nafion); $R_1$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl; $R_2$ represents alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl; $R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)=C(R_8)_2$, —$C\equiv CR_8$, —$CH(R_8)_2$, or —$C(R_8)_3$; and $R_8$ represents independently for each occurrence —$(CH_2)_n$—$CH_3$, cycloalkyl, aryl, or heteroaryl.

In certain embodiments, the invention relates to any of the aforementioned methods, wherein the salt is represented by

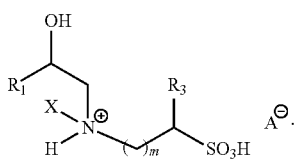

In certain embodiments, the invention relates to any of the aforementioned methods, wherein the salt is represented by

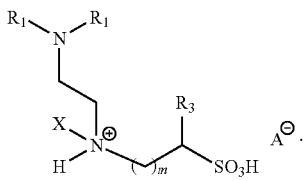

In certain embodiments, the invention relates to any of the aforementioned methods, wherein $R_1$ represents n-hexyl, 1,5-dimethylhexyl, 2-ethylhexyl, 2-heptyl, isopropyl, isobutyl, or 2-hydroxyethyl; and $R_3$ represents H or methyl.

In certain embodiments, the invention relates to any of the aforementioned methods, wherein $R_1$ represents n-hexyl, 1,5-dimethylhexyl, 2-ethylhexyl, 2-heptyl, isopropyl, isobutyl, or 2-hydroxyethyl; $R_3$ represents H or methyl; and m is 2 or 3.

In certain embodiments, the invention relates to any of the aforementioned methods, wherein $R_1$ represents alkyl, aryl or aralkyl; and $R_3$ represents H or methyl.

In certain embodiments, the invention relates to any of the aforementioned methods, wherein $R_1$ represents alkyl, aryl or aralkyl; $R_3$ represents H or methyl; and m is 2 or 3.

In certain embodiments, the invention relates to a method of releasing a gas, comprising the step of heating a salt; wherein the salt is represented by

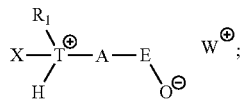

wherein, independently for each occurrence,

X represents $-CO_2^{-1}$, $-CS_2^{-1}$, $-SO^{-1}$ or $-NO_2^{-1}$;

W represents an ammonium cation, a phosponium cation, a heterocyclic cation, an alkali metal cation or an alkaline earth metal cation;

T represents N or P;

E represents $-C(=O)-$ or $-S(=O)_2-$;

A represents an aryl or heteroaryl diradical;

$R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_8$ represents independently for each occurrence $-(CH_2)_n-CH_3$, cycloalkyl, aryl, or heteroaryl;

m represents independently for each occurrence an integer in the range 1-10 inclusive; and n represents independently for each occurrence an integer in the range 1-10 inclusive.

In certain embodiments, the invention relates to any of the aforementioned methods, wherein X is $-CO_2^{-1}$.

In certain embodiments, the invention relates to any of the aforementioned methods, wherein W is an ammonium, pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium.

In certain embodiments, the invention relates to any of the aforementioned methods, wherein W is

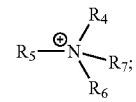

$R_4$ and $R_5$ represent independently for each occurrence alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, $-(CH_2)_n-R_8$, $-C(R_8)=C(R_8)_2$, $-C\equiv CR_8$, $-CH(R_8)_2$, or $-C(R_8)_3$; or $R_4$ and $R_5$ taken together with the nitrogen to which they are attached form a five-, six-, or seven-membered heterocyclic ring; $R_6$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, $-(CH_2)_n-R_8$, $-C(R_8)=C(R_8)_2$, $-C\equiv CR_8$, $-CH(R_8)_2$, or $-C(R_8)_3$; and $R_7$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, $-(CH_2)_n-R_8$, $-C(R_8)=C(R_8)_2$, $-C\equiv CR_8$, $-CH(R_8)_2$, or $-C(R_8)_3$.

In certain embodiments, the invention relates to any of the aforementioned methods, wherein T represents N.

In certain embodiments, the invention relates to any of the aforementioned methods, wherein E represents $-C(=O)-$. In certain embodiments, the invention relates to any of the aforementioned methods, wherein E represents $-S(=O)_2-$.

In certain embodiments, the invention relates to any of the aforementioned methods, wherein $R_1$ is alkyl, aryl or aralkyl. In certain embodiments, the invention relates to any of the aforementioned methods, wherein $R_1$ is alkyl.

In certain embodiments, the invention relates to any of the aforementioned methods, wherein $R_3$ is hydrogen or alkyl.

In certain embodiments, the invention relates to any of the aforementioned methods, wherein $R_4$, $R_5$, $R_6$, and $R_7$ is alkyl.

In certain embodiments, the invention relates to any of the aforementioned methods, wherein A is an aryl diradical. In certain embodiments, the invention relates to any of the aforementioned methods, wherein A is an benzene diradical.

In certain embodiments, the invention relates to any of the aforementioned methods, wherein T represents N; $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-CH_2CH(OH)-R_8$, —$(CH_2)_n$—$R_8$, —$C(R_8)$=$C(R_8)_2$, —C≡$CR_8$, —$CH(R_8)_2$, or —$C(R_8)_3$; and A is an aryl diradical.

In certain embodiments, the invention relates to any of the aforementioned methods, wherein T represents N; $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)$=$C(R_8)_2$, —C≡$CR_8$, —$CH(R_8)_2$, or —$C(R_8)_3$; and A is an aryl diradical; and $R_4$, $R_5$, $R_6$, and $R_7$ represent independently for each occurrence methyl, ethyl, or n-butyl.

In certain embodiments, the invention relates to any of the aforementioned methods, wherein $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)$=$C(R_8)_2$, —C≡$CR_8$, —$CH(R_8)_2$, or —$C(R_8)_3$; and A is an aryl diradical.

In certain embodiments, the invention relates to any of the aforementioned methods, wherein $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)$=$C(R_8)_2$, —C≡$CR_8$, —$CH(R_8)_2$, or —$C(R_8)_3$; and A is an aryl diradical; and $R_4$, $R_5$, $R_6$, and $R_7$ represent independently for each occurrence methyl, ethyl, or n-butyl.

In certain embodiments, the invention relates to any of the aforementioned methods, wherein $R_4$, $R_5$, $R_6$, and $R_7$ represent independently for each occurrence methyl, ethyl, or n-butyl.

In certain embodiments, the invention relates to any of the aforementioned methods, wherein the salt is represented by

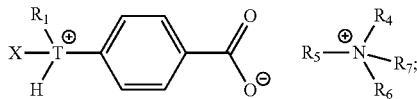

$R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl —$CH_2CH(OH)$—$R_8$ or —$CH_2CHN(R_8)_2$; $R_4$, $R_5$, $R_6$, and $R_7$ represent independently for each occurrence methyl, ethyl, or n-butyl; and $R_8$ represents alkyl, aryl or aralkyl.

In certain embodiments, the invention relates to any of the aforementioned methods, wherein $R_1$ represents alkyl, aryl or aralkyl. In certain embodiments, the invention relates to any of the aforementioned methods, wherein $R_1$ represents —$CH_2CH(OH)$—$R_8$ or —$CH_2CHN(R_8)_2$. In certain embodiments, the invention relates to any of the aforementioned methods, wherein $R_1$ represents alkyl, aryl or aralkyl; and $R_4$, $R_5$, $R_6$, and $R_7$ represent independently for each occurrence methyl, ethyl, or n-butyl.

In certain embodiments, the invention relates to a method of releasing a gas, comprising the step of heating a salt; wherein the salt is represented by

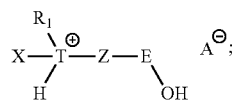

wherein, independently for each occurrence,
X represents —$CO_2^{-1}$, —$CS_2^{-1}$, —$SO_2^{-1}$ or —$NO_2^{-1}$;

A represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)-(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, tris(perfluoroalkyl)trifluorophosphate anion, or an anionic site of a cation-exchange resin;

T represents N or P;

E represents —C(=O)— or —S(=O)$_2$—;

Z represents an aryl or heteroaryl diradical;

$R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;

$R_8$ represents independently for each occurrence —$(CH_2)_n$—$CH_3$, cycloalkyl, aryl, or heteroaryl;

m represents independently for each occurrence an integer in the range 1-10 inclusive; and n represents independently for each occurrence an integer in the range 1-10 inclusive.

In certain embodiments, the invention relates to any of the aforementioned methods, wherein X is —$CO_2^{-1}$.

In certain embodiments, the invention relates to any of the aforementioned methods, wherein A represents $I^{-1}$, $Br^{-1}$, $Cl^{-1}$, $HSO_4^{-1}$, $CH_3SO_3^{-1}$, $NO_3^{-1}$, $ClO_3^{-1}$, $FSO_3^{-1}$, $CF_3SO_3^{-1}$, $(CF_3SO_2)_2N^{-1}$, tris(perfluoroalkyl)-trifluorophosphate (FAP) anions, or a tetrafluoroethylene-perfluoro-3,6-dioxa-4-methyl-7-octenesulfonic acid copolymer (Nafion).

In certain embodiments, the invention relates to any of the aforementioned methods, wherein T represents N.

In certain embodiments, the invention relates to any of the aforementioned methods, wherein E represents —C(=O)—.

In certain embodiments, the invention relates to any of the aforementioned methods, wherein E represents —S(=O)$_2$—.

In certain embodiments, the invention relates to any of the aforementioned methods, wherein $R_1$ is alkyl, aryl or aralkyl.

In certain embodiments, the invention relates to any of the aforementioned methods, wherein $R_1$ is alkyl.

In certain embodiments, the invention relates to any of the aforementioned methods, wherein $R_3$ is hydrogen or alkyl.

In certain embodiments, the invention relates to any of the aforementioned methods, wherein Z is an aryl diradical. In certain embodiments, the invention relates to any of the aforementioned methods, wherein Z is an benzene diradical.

In certain embodiments, the invention relates to any of the aforementioned methods, wherein $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$CH_2CH(OH)$—$R_8$, —$(CH_2)_n$—$R_8$, —$C(R_8)$=$C(R_8)_2$, —C≡$CR_8$, —$CH(R_8)_2$, or —$C(R_8)_3$; and Z is an aryl diradical.

In certain embodiments, the invention relates to any of the aforementioned methods, wherein T represents N; $R_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —CH$_2$CH(OH)—R$_8$, —(CH$_2$)$_n$—R$_8$, —C(R$_8$)=C(R$_8$)$_2$, —C≡CR$_8$, —CH(R$_8$)$_2$, or —C(R$_8$)$_3$; and Z is an aryl diradical.

In certain embodiments, the invention relates to any of the aforementioned methods, wherein the salt is represented by

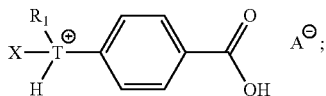

R$_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl —CH$_2$CH(OH)—R$_8$ or —CH$_2$CHN(R$_8$)$_2$; and R$_8$ represents alkyl, aryl or aralkyl.

In certain embodiments, the invention relates to any of the aforementioned methods, wherein R$_1$ represents alkyl, aryl or aralkyl. In certain embodiments, the invention relates to any of the aforementioned methods, wherein R$_1$ represents —CH$_2$CH(OH)—R$_8$ or —CH$_2$CHN(R$_8$)$_2$.

EXEMPLIFICATION

The invention now being generally described, it will be more readily understood by reference to the following examples which are included merely for purposes of illustration of certain aspects and embodiments of the present invention, and are not intended to limit the invention.

Example 1

Synthesis of Zwitterions for Propanesultone and 2,4-Butanesultone Compounds

The sultone is dissolved in 50 mL toluene. The amine is added slowly and the solution stirred overnight. The resulting solid is filtered by vacuum filtration. The crude product is rotary evaporated and further dried under vacuum. The salt is recrystallized from hot methanol and dried under vacuum. The product is characterized by $^1$H and $^{13}$C NMR.

Example 2

Synthesis of Zwitterions for 1,4-Butanesultone Compounds

The sultone is dissolved in 50 mL toluene. The amine is added slowly and the solution refluxed overnight. The resulting solid is filtered by vacuum filtration. The crude product is rotary evaporated and further dried under vacuum. The salt is recrystallized from hot methanol and dried under vacuum. The product is characterized by $^1$H and $^{13}$C NMR.

Example 3

Synthesis of Ammonium Salts

The zwitterion is dissolved in 10 mL water or methanol Ammonium hydroxide is added and the solution stirred for 30 min. The crude product is rotary evaporated and further dried under vacuum. The product is characterized by $^1$H and $^{13}$C NMR Example 4

Water Saturation Experiments

Samples of select salts (mostly the resinous/plastic/gel-like materials) were azeotropically dried with benzene, placed into open vials then stored in vacuo over P$_2$O$_5$(s) for 1 week. The "dry" mass of each sample was then determined. The open sample vials were then stored in a sealed in a container above a water reservoir, and the salt masses re-determined and the physical state of each material qualitatively assessed at 1, 4, 7 and 14 day intervals. The resulting mass changes were tabulated, and the molar water uptake as a function of time are shown graphically for each salt (see FIGS. 7 and 8).

Example 5

Reversible Capture of CO$_2$ with a Resinous Material

In order to demonstrate the potential utility of the adhering nature of the plastic or resinous materials, [1B2A3A] was used to create a prototype pass-through device for reversible CO$_2$ capture (FIG. 2). On exposing the resin to a slow flow of CO$_2$ for 12 h, it became opaque and frosted in appearance, consistent with CO$_2$ absorption (vide infra). Subsequent passage of hot water (~80° C.) through the coil while subjecting the sample to mechanical vacuum resulted in CO$_2$ extrusion and a return of the resin to its pre-exposure appearance. Remarkably, this compound and the others like it are the first non-polymeric plastic or resinous materials used to capture CO$_2$, making them potentially valuable compliments to SAWD technology (see Etoh, T. et al. Intersociety Conference on Environmental Systems; Society of Automotive Engineers: Seattle, Wash., 1987; Technical Paper 871516).

Example 6

Synthesis of Zwitterions for Propanesultone and 2,4-Butanesultone Compounds

The sultone is dissolved in 50 mL toluene. The amine is added slowly and the solution stirred overnight. The resulting solid is filtered by vacuum filtration. The crude product is rotary evaporated and further dried under vacuum. The salt is recrystallized from hot methanol and dried under vacuum. The product is characterized by $^1$H and $^{13}$C NMR.

Example 7

Synthesis of Zwitterions for 1,4-Butanesultone Compounds

The sultone is dissolved in 50 mL toluene. The amine is added slowly and the solution refluxed overnight. The resulting solid is filtered by vacuum filtration. The crude product is rotary evaporated and further dried under vacuum. The salt is recrystallized from hot methanol and dried under vacuum. The product is characterized by $^1$H and $^{13}$C NMR.

Example 8

Synthesis of Ammonium Salts

The zwitterion is dissolved in 10 mL water or methanol Ammonium hydroxide is added and the solution stirred for 30 min. The crude product is rotary evaporated and further dried under vacuum. The product is characterized by $^1$H and $^{13}$C NMR.

Example 9

Synthesis of the Zwitterion of Propane Sultone and 3-(Diethylamino)Propylamine

A 500 mL round-bottomed flask equipped with a stir bar, reflux condenser and drying tube was charged with 5.01 g propane sultone (41.0 mmol) and 150 mL of reagent grade toluene. To this solution was then added 5.34 g of 3-(diethylamino) propylamine (41.0 mmol). The solution was stirred at ambient temperature for seven days at which time a white precipitate was observed. The white precipitate was filtered and washed with diethyl ether (2×, 100 mL) and dried in vacuo, leaving a white solid product (6.63 g, 64%).

Example 10

Synthesis of 3-(Diethylamino)-1-(Propyl-3-Sulfonyl) Propylamoonium Bistrifluoromethanesulfoimidate A 50 mL beaker was charged with 2.69 g of zwitterion product from Example 9 (10.7 mmol), 2.3 mL of bistrifluoromethanesulfoimide (4.2 M, 9.6 mmol) and 5 ml deionized water. A clear, light yellow solution was observed. The solution was filtered and the water removed in vacuo, leaving a light yellow, viscous liquid product (5.02 g, 98%).

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

INCORPORATION BY REFERENCE

All of the US patent and US patent application Publications cited herein are hereby incorporated by reference.

I claim:
1. A salt represented by:

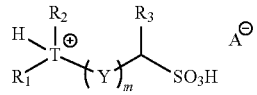

wherein, independently for each occurrence,
A represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)-(fluoroalkylcarbonyl)amide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, tris(perfluoroalkyl)trifluorophosphate anion, or an anionic site of a cation-exchange resin;
T represents N or P;
Y represents $CH_2$, CHF, $CF_2$ or Z—O—Z;
Z represents $CH_2$, CHF or $CF_2$;
$R_1$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro,sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;
$R_2$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;
$R_3$ represents hydrogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, bicyclic ring, tricyclic ring, bicyclic or tricyclic fused ring, —$(CH_2)_n$—$R_8$, —C(=O)O$R_8$, —C(=O)N$(R_8)_2$, —C(=O)S$R_8$, —C(=O)$R_8$, —C(=N$R_8$)$R_8$, —C(=S)$R_8$, —C$(R_8)$=C$(R_8)_2$, —C≡C$R_8$, —CH$(R_8)_2$, —C$(R_8)_3$, or —$(CH_2)_n$—$NH_2$;
$R_4$ and $R_5$ represent independently for each occurrence alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —$(CH_2)_n$—$R_8$, —C$(R_8)$=C$(R_8)_2$, —C≡C$R_8$, —CH$(R_8)_2$, or —C$(R_8)_3$; or $R_4$ and $R_5$ taken together with the nitrogen to which they are attached form a five-, six-, or seven-membered heterocyclic ring;
$R_6$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —$(CH_2)_n$—$R_8$, —C$(R_8)$=C$(R_8)_2$, —C≡C$R_8$, —CH$(R_8)_2$, or —C$(R_8)_3$;
$R_7$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —$(CH_2)_n$—$R_8$, —C$(R_8)$=C$(R_8)_2$, —C≡C$R_8$, —CH$(R_8)_2$, or —C$(R_8)_3$;
$R_8$ represents independently for each occurrence —$(CH_2)_n$—$CH_3$, cycloalkyl, aryl, or heteroaryl;
m represents independently for each occurrence an integer in the range 1-10 inclusive; and
n represents independently for each occurrence an integer in the range 1-10 inclusive;
or a salt represented by:

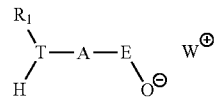

wherein, independently for each occurrence,
W represents an ammonium cation, a phosponium cation, or a heterocyclic cation;
T represents N or P;
E represents —C(=O)— or —S(=O)$_2$—;
A represents an aryl or heteroaryl diradical;
R$_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;
R$_8$ represents independently for each occurrence —(CH$_2$)$_n$—CH$_3$, cycloalkyl, aryl, or heteroaryl;
m represents independently for each occurrence an integer in the range 1-10 inclusive; and
n represents independently for each occurrence an integer in the range 1-10 inclusive;
or a salt represented by:

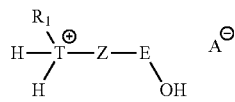

wherein, independently for each occurrence,
A represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)-(fluoroalkylcarbonyl)amide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, tris(perfluoroalkyl)trifluorophosphate anion, or an anionic site of a cation-exchange resin;
T represents N or P;
E represents —C(=O)— or —S(=O)$_2$—;
Z represents an aryl or heteroaryl diradical;
R$_1$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl; wherein said alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, or arylcycloalkyl may be substituted with 1 to 3 substituents selected from the group consisting of halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aryl, heteroaryl, fluoroalkyl and cyano;
R$_8$ represents independently for each occurrence —(CH$_2$)$_n$—CH$_3$, cycloalkyl, aryl, or heteroaryl;
m represents independently for each occurrence an integer in the range 1-10 inclusive; and
n represents independently for each occurrence an integer in the range 1-10 inclusive.

2. The salt of claim 1, wherein W is an ammonium, pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium.

3. The salt of claim 1, wherein W is

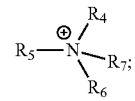

R$_4$ and R$_5$ represent independently for each occurrence alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —(CH$_2$)$_n$—R$_8$, —C(R$_8$)=C(R$_8$)$_2$, —C≡CR$_8$, —CH(R$_8$)$_2$, or —C(R$_8$)$_3$; or R$_4$ and R$_5$ taken together with the nitrogen to which they are attached form a five-, six-, or seven-membered heterocyclic ring; R$_6$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —(CH$_2$)$_n$—R$_8$, —C(R$_8$)=C(R$_8$)$_2$, —C≡CR$_8$, —CH(R$_8$)$_2$, or —C(R$_8$)$_3$; and R$_7$ represents alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, arylcycloalkyl, —(CH$_2$)$_n$—R$_8$, —C(R$_8$)=C(R$_8$)$_2$, —C≡CR$_8$, —CH(R$_8$)$_2$, or —C(R$_8$)$_3$.

4. The salt of claim 1, wherein T represents N.

5. The salt of claim 1, wherein Y represents CH$_2$, CHF or CF$_2$.

6. The salt of claim 1, wherein only one Y represents Z—O—Z.

7. The salt of claim 1, wherein only one Y represents Z—O—Z; and Z is CH$_2$.

8. The salt of claim 1, wherein only one Y represents Z—O—Z; and Z is CF$_2$.

9. The salt of claim 1, wherein R$_1$ is hydrogen.

10. The salt of claim 1, wherein R$_1$ represents alkyl, fluoroalkyl, cycloalkyl, heterocycloalkyl, alkenyl, cycloalkenyl, heterocycloalkenyl, alkynyl, aryl, heteroaryl, aralkyl, or heteroaralkyl.

11. The salt of claim 1, wherein R$_2$ is alkyl, aryl or aralkyl.

12. The salt of claim 1, wherein R$_3$ is hydrogen or alkyl.

13. The salt of claim 1, wherein m is 2 or 3.

14. The salt of claim 1, wherein the salt is represented by

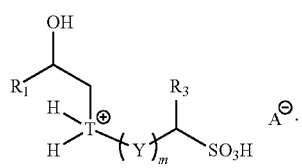

15. The salt of claim 1, wherein the salt is represented by

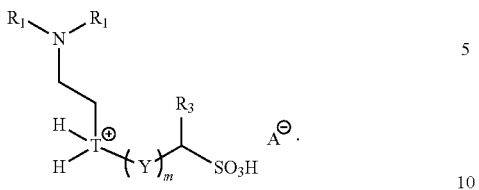

16. The salt of claim 1, wherein A represents $HSO_4^{-1}$, $CH_3SO_3^{-1}$, $NO_3^{-1}$, $ClO_3^{-1}$, $FSO_3^{-1}$, $CF_3SO_3^{-1}$, $(CF_3SO_2)_2N^{-1}$, tris(perfluoroalkyl)-trifluorophosphate anions, or a tetrafluoroethylene-perfluoro-3,6-dioxa-4-methyl-7-octene-sulfonic acid copolymer.

17. The salt of claim 1, wherein E represents —C(=O)—.

18. The salt of claim 1, wherein E represents —S(=O)$_2$—.

19. The salt of claim 1, wherein A is an aryl diradical.

20. A method of sequestering a gas, comprising contacting the gas with a salt of claim 1.

21. A method of releasing a gas, comprising the step of heating a composition comprising a gas dissolved in a salt; wherein the salt is the salt of claim 1.

* * * * *